(12) United States Patent
Nilsson et al.

(10) Patent No.: US 11,975,130 B2
(45) Date of Patent: May 7, 2024

(54) SYSTEM AND A METHOD FOR RENAL REPLACEMENT THERAPY

(71) Applicant: GAMBRO LUNDIA AB, Lund (SE)

(72) Inventors: Roger Nilsson, Höör (SE); Björn Ericson, Lund (SE); Jan Sternby, Lund (SE); Thomas Hertz, Lund (SE); Olof Jansson, Vellinge (SE); Sture Hobro, Lund (SE); Anders Wallenborg, Bjärr (SE); Jonas Fors, Malmö (SE); Henrik Lindgren, Genarp (SE); Annmargret Håkansson, Kågeröd (SE)

(73) Assignee: GAMBRO LUNDIA AB, Lund (SE)

( * ) Notice: Subject to any disclaimer, the term of this patent is extended or adjusted under 35 U.S.C. 154(b) by 625 days.

(21) Appl. No.: 16/621,629

(22) PCT Filed: Jun. 21, 2018

(86) PCT No.: PCT/EP2018/066522
§ 371 (c)(1),
(2) Date: Dec. 11, 2019

(87) PCT Pub. No.: WO2019/002067
PCT Pub. Date: Jan. 3, 2019

(65) Prior Publication Data
US 2020/0155745 A1 May 21, 2020

(30) Foreign Application Priority Data
Jun. 28, 2017 (SE) .................................. 1750839-1

(51) Int. Cl.
*A61M 1/16* (2006.01)
*A61M 1/30* (2006.01)
*A61M 1/36* (2006.01)

(52) U.S. Cl.
CPC .......... *A61M 1/1609* (2014.02); *A61M 1/304* (2014.02); *A61M 1/367* (2013.01)

(58) Field of Classification Search
CPC .... A61M 1/1609; A61M 1/304; A61M 1/367; A61M 1/307; A61M 1/341; A61M 1/3403; A61M 1/3434
See application file for complete search history.

(56) References Cited

U.S. PATENT DOCUMENTS 6,890,315 B1    5/2005 Levin et al.
9,061,099 B2 *  6/2015 Gerber ................ A61M 1/1601
(Continued)

FOREIGN PATENT DOCUMENTS

AU    2012259459 B2    6/2016
CA       2647919 A1    1/2009
(Continued)

OTHER PUBLICATIONS

International Search Report; International Application No. PCT/EP2018/066522; dated Oct. 29, 2018; 4 Pages.
(Continued)

*Primary Examiner* — Susan S Su
*Assistant Examiner* — Ted Yang
(74) *Attorney, Agent, or Firm* — K&L Gates LLP (57) ABSTRACT

A system and a method for renal replacement therapy includes a blood treatment unit connected to a blood circuit and a dialysis fluid circuit, the system further including a control unit configured to control the system according to control instructions during a treatment, so as to determine a system parameter value and an indication of membrane fouling of the membrane, and activate an automatic antifouling measure that includes a temporary change of the flow rate in the blood circuit and a temporary decrease of the
(Continued)

ultrafiltration rate wherein a timing of the temporary change and a timing of the temporary reduction are synchronized.

28 Claims, 4 Drawing Sheets

(56) References Cited

U.S. PATENT DOCUMENTS

| | | | |
|---|---|---|---|
| 2005/0230314 A1* | 10/2005 | Kim | A61M 1/3607 210/646 |
| 2008/0251433 A1* | 10/2008 | Kim | A61M 1/3612 210/108 |
| 2010/0264086 A1 | 10/2010 | Noack et al. | |
| 2012/0273415 A1* | 11/2012 | Gerber | A61M 1/361 210/741 |
| 2012/0273416 A1 | 11/2012 | Wegener et al. | |
| 2013/0211730 A1* | 8/2013 | Wolff | G16H 20/40 702/19 |
| 2013/0274642 A1 | 10/2013 | Soykan et al. | |
| 2013/0303961 A1* | 11/2013 | Wolff | A61M 1/342 604/5.04 |
| 2015/0343134 A1 | 12/2015 | Tschulena et al. | |
| 2017/0095772 A1* | 4/2017 | Kim | B01D 69/02 |

FOREIGN PATENT DOCUMENTS

| | | | | |
|---|---|---|---|---|
| JP | 2004016619 A | * | 1/2004 | |
| WO | WO-03051427 A1 | * | 6/2003 | A61M 1/16 |
| WO | WO 2014/095073 A1 | | 6/2014 | |

OTHER PUBLICATIONS

Written Opinion of the International Searching Authority; International Application No. PCT/EP2018/066522; dated Oct. 29, 2018; 9 Pages.

* cited by examiner

SYSTEM AND A METHOD FOR RENAL REPLACEMENT THERAPY

PRIORITY CLAIM

The present application is a National Phase of International Application No. PCT/EP2018/066522, filed Jun. 21, 2018, which claims priority to SE Application No. 1750839-1, filed Jun. 28, 2017, the entire contents of each of which are incorporated herein by reference and relied upon.

TECHNICAL FIELD

The present disclosure relates to the field of renal replacement therapy for extracorporeal treatment of blood, and in particular to a system for renal replacement therapy and a method for managing membrane fouling of a blood treatment unit in a system for renal replacement therapy.

BACKGROUND

Renal replacement therapy systems are used for patients that for some reason have to treat their blood outside their bodies. An extracorporeal blood treatment can be used to extract undesirable substances or molecules from the patient's blood, and, if necessary, to add desirable substances or molecules to the blood. The extracorporeal blood treatment is accomplished by passing blood through a blood treatment unit, e.g. a dialyzer or a hemofilter. A membrane separates the treatment unit into a blood compartment and a fluid compartment. Blood withdrawn from the patient is introduced into the blood compartment and flows past the membrane. The membrane is semipermeable to selectively allow matter in the blood to flow across the membrane from the blood compartment into the fluid compartment. The membrane also selectively allows matter in the fluid compartment to flow across the membrane into the blood compartment, depending on the type of treatment.

A number of different types of extracorporeal blood treatments may be performed. In an ultrafiltration (UF) treatment, undesirable matter is removed from the blood by convection across the membrane into the fluid compartment. In a hemofiltration (HF) treatment, the blood flows past the membrane as in a UF treatment and desirable matter is added to the blood, typically by dispensing a fluid into the blood either before and/or after it passes through the treatment unit and before it is returned to the patient. In a hemodialysis (HD) treatment, a secondary fluid containing desirable matter is introduced into the fluid compartment of the treatment unit. Undesirable matter from the blood crosses the membrane into the secondary fluid and desirable matter from the secondary fluid may cross the membrane into the blood. In a hemodiafiltration (HDF) treatment, blood and secondary fluid exchange matter as in HD, and, in addition, matter is added to the blood, typically by dispensing a fluid into the treated blood before its return to the patient as in HF.

Coagulation of the blood, also referred to as clotting, is usually reduced by using anti-coagulants such as heparin. However, during treatment material from the blood such as clotted blood, proteins etc. may start to clog the membrane of the treatment unit. This phenomenon may be referred to as membrane fouling. The effects on the membrane are a progressive decline in flux and a change of membrane selectivity. Membrane fouling is mainly caused by concentration polarization and protein adsorption or deposition on the surface or in its pores. Concentration polarization is a result of a concentration gradient due to solute accumulation near the membrane surface. This solute accumulation is also referred to as a secondary membrane. Protein adsorption or deposition on the surface or in its pores is caused by proteins that are adsorbed or trapped in the pores of the membrane, and thereby changes the membrane properties. When regions of the membrane start to become less effective, action has to be taken to maintain the same efficiency of the treatment.

Membrane fouling has previously been managed by rinsing the blood circuit and changing filter. However, these procedures are time consuming and the treatment has to be stopped.

From WO2014/095073A1 it is known to control the transmembrane pressure (TMP), haematocrit (HCT) or blood density by regulating at least one of the infusion speeds of the substitution fluids added upstream and/or downstream the treatment unit. Thereby a built-up limiting secondary membrane on the membrane in the blood treatment unit may be kept constant to thereby achieve a constant purifying effect of the blood. For example, in the case of a high TMP or a high HCT value of the blood, the infusion rate of the upstream added substitution fluid can be increased until the desired values of the controlled values are reached. However, dilution of the blood upstream the treatment unit changes the blood composition and its effect on the treatment efficiency is debated.

SUMMARY

In HF and HDF treatments, especially high volume HF and HDF treatments, it is in most cases desired to add as much as possible of the substitution fluid downstream of the treatment unit, because the blood thereby becomes more concentrated in the treatment unit with a positive effect on the treatment efficiency.

However, the membrane fouling limits the water permeability through the membrane, and the decreased permeability decreases the convective volume that can be achieved during treatment.

Thus, there is a need for an improved method for managing fouling of a blood treatment unit in HF, HD and HDF treatments.

The objective of the disclosure is to alleviate at least some of the drawbacks with the prior art. It is a further objective to provide a system and a method for managing membrane fouling of a blood treatment unit. It is a still further objective to provide a system and a method for managing membrane fouling of a blood treatment unit in HF, HD or HDF treatments, and in particular high volume post-dilution HF and HDF treatments. It is a still further objective to provide a system and a method for managing membrane fouling such that the efficiency of the treatment is increased. It is another objective to reduce or eliminate the use of heparin or other anti-coagulants during treatment. Some patients cannot sustain anticoagulation drugs and for these patients so called Heparin Free treatments are used. In such treatments, the membrane will be particularly vulnerable to fouling.

These objectives and others are at least partly achieved by the system and the method according to the independent claims, and by the embodiments according to the dependent claims.

According to a first aspect, the disclosure relates to a system for renal replacement therapy comprising a blood treatment unit arranged to be connected to a blood circuit for extracorporeal circulation of blood comprising an arterial line and a venous line. The blood treatment unit comprises a blood compartment and a fluid compartment separated by a semipermeable membrane. The system further comprises a blood pump arranged to create a blood flow rate $Q_B$ in the arterial line, a dialysis fluid circuit comprising a supply line arranged for supply of a dialysis fluid to the fluid compartment of the blood treatment unit, and a drain line arranged for withdrawal of used fluid from the fluid compartment of the blood treatment unit. The system further comprises at least one fluid pump arranged to create a fluid flow rate in the dialysis fluid circuit and a control unit configured to control the system according to control instructions. The control instructions comprise to, during a treatment, determine a system parameter value and an indication of membrane fouling of the membrane based on a predetermined criterion for the system parameter value, and thereby activate an automatic anti-fouling measure comprising a temporary change of the flow rate in the blood circuit upstream the blood treatment unit and a temporary decrease of an ultrafiltration rate across the semipermeable membrane, wherein a timing of the temporary change of the flow rate in the blood circuit and a timing of the temporary decrease of the ultrafiltration rate are synchronized.

With the described system, the membrane fouling is counteracted, and it is possible to achieve an overall more efficient treatment. The membrane thus becomes more permeable through the treatment whereby the ultrafiltration rate in HF and HDF treatments can be maintained, i.e. it is possible to keep a higher ultrafiltration rate through the treatment. By synchronizing timing of the temporary change of the flow rate in the blood circuit and a timing of the temporary decrease of the ultrafiltration rate, it is possible to remove parts or all of the secondary membrane that has been built up on the semi-permeable membrane in the blood compartment in an efficient way with small or no changes to the on-going treatment. The system gives the advantage of a treatment with a high efficiency with low or short influence on the treatment properties. Further, less or no heparin may be used which is beneficial for most patients and especially for patients who cannot use heparin.

According to some embodiments, the predetermined criterion comprises a limit value of the system parameter value. The control instructions comprise to compare the determined system parameter value with the limit value of the system parameter, and to control the anti-fouling measure based on a result of the comparison.

According to some embodiments, the control instructions comprise to maintain the automatic anti-fouling measure for a certain time period $\Delta t1$ after activation of the same, e.g. based on the result of the comparison.

According to some embodiments, the system comprises a pre-dilution line arranged for infusion of substitution fluid upstream the treatment unit, and flow control means arranged to regulate a pre-dilution flow rate $Q_{pre}$ of substitution fluid in the pre-dilution line, wherein the temporary change of the flow rate in the blood circuit comprises to infuse a volume of substitution fluid via the pre-dilution line to the blood circuit.

As a further explanation: When adding fluid upstream the blood treatment unit, the blood becomes thinner and much easier to filtrate. An ultrafiltration rate of the system may then be increased. However, since the blood is diluted, the "system clearance", i.e. the clearance of undiluted blood, will be reduced by the pre-dilution factor. The system according to the disclosure enables an average high ultrafiltration rate, while at the same time delivering an average high system clearance.

According to some embodiments, the temporary change of the flow rate in the blood circuit comprises to decrease or stop the velocity of the blood pump.

According to some embodiments, the temporary change of the flow rate in the blood circuit comprises to increase the velocity of the blood pump.

According to some embodiments, the temporary decrease of the ultrafiltration rate across the semipermeable membrane is adapted to cause a backwash comprising to infuse a volume of dialysis fluid from the fluid compartment into the blood compartment through the semipermeable membrane.

According to some embodiments, the temporary decrease of the ultrafiltration rate across the semipermeable membrane is adapted to cause the ultrafiltration rate to be zero.

According to some embodiments, the control instructions comprises to control the ultrafiltration rate after an anti-fouling measure, such that the temporary decrease of the ultrafiltration rate across the semipermeable membrane is compensated for during the remaining treatment.

According to some embodiments, the control instructions comprise to control the timing of the temporary change of the flow rate in the blood circuit and to control the timing of the temporary decrease of ultrafiltration rate such that the temporary change in the flow rate in the blood circuit and the temporary decrease of ultrafiltration rate have an impact on the blood treatment unit simultaneously during at least one time period $\Delta t2$.

According to some embodiments, the control instructions comprise to control the timing of the temporary change of the flow rate in the blood circuit and to control the timing of the temporary decrease of ultrafiltration rate such that the temporary decrease of ultrafiltration rate has an earlier impact on the blood treatment unit than the impact the temporary change of the flow rate in the blood circuit has to the blood treatment unit.

According to some embodiments, the control instructions comprise to control the timing of the temporary change of the flow rate in the blood circuit and to control the timing of the temporary decrease of ultrafiltration rate such that the temporary change of the flow rate in the blood circuit has an earlier impact on the blood treatment unit than the temporary decrease of ultrafiltration rate.

According to some embodiments, the system parameter to be determined is based on one or several of a current $I_B$ consumed by a motor of the blood pump, a system pressure $P_{bi}$, a transmembrane pressure, TMP, across the blood treatment unit, an infusion flow rate $Q_{IR}$, a post-dilution flow rate $Q_{post}$, a haemoconcentration of the blood $C_E$, an ultrafiltration, UF, coefficient, a clearance K and/or another efficiency parameter of the treatment. The system parameter to be determined may also be determined based on a combination of any of the specified parameters.

According to a second aspect, the disclosure relates to a method for use in a renal replacement therapy system comprising a blood treatment unit arranged to be connected to a blood circuit for extracorporeal circulation of blood comprising an arterial line and a venous line, wherein the blood treatment unit comprises a blood compartment and a fluid compartment separated by a semipermeable membrane, a blood pump arranged to create a blood flow rate $Q_B$ in the arterial line, a dialysis fluid circuit comprising a supply line arranged for supply of a dialysis fluid to the fluid compartment of the blood treatment unit, and a drain line arranged for withdrawal of used fluid from the fluid compartment of the blood treatment unit; at least one fluid pump arranged to create a fluid flow rate in the dialysis fluid circuit; and a control unit. The method comprises, during a treatment:

determining a system parameter value;

determining an indication of membrane fouling of the membrane based on a predetermined criterion for the system parameter value; and thereby activating an automatic anti-fouling measure comprising temporarily changing the flow rate in the blood circuit upstream the blood treatment unit and temporarily decreasing an ultrafiltration rate across the semipermeable membrane, and synchronizing timing of the temporary change of the flow rate in the blood circuit and timing of the temporary decrease of the ultrafiltration rate.

The same described advantages as for the system may be achieved by the method.

According to some embodiments, the predetermined criterion comprises a limit value of the system parameter value, and the method comprises comparing the determined system parameter value with the limit value of the system parameter, and controlling the anti-fouling measure based on a result of the comparison.

According to some embodiments, the method comprises maintaining the automatic anti-fouling measure for a certain time period $\Delta t1$ after activation of the same, e.g. based on the result of the comparison.

According to some embodiments, the temporary change of the flow rate in the blood circuit comprises infusing a volume of substitution fluid via a pre-dilution line to the blood circuit upstream the treatment unit.

According to some embodiments, the temporary change of the flow rate in the blood circuit comprises decreasing or stopping the velocity of the blood pump.

According to some embodiments, the temporary change of the flow rate in the blood circuit comprises increasing the velocity of the blood pump.

According to some embodiments, the temporary decreasing of the ultrafiltration rate causes a backwash comprising infusing a volume of dialysis fluid from the fluid compartment into the blood compartment through the semipermeable membrane.

According to some embodiments, the temporary decreasing of the ultrafiltration rate across the semipermeable membrane causes the ultrafiltration rate to be zero.

According to some embodiments, the method comprises controlling the ultrafiltration rate after an anti-fouling measure, such that the temporary decrease of the ultrafiltration rate across the semipermeable membrane is compensated for during the remaining treatment.

According to some embodiments, the method comprises controlling the timing of the temporary change of the flow rate in the blood circuit and controlling the timing of the temporary decreasing of the ultrafiltration rate such that the temporary change of the flow rate in the blood circuit and the temporary decreasing of the ultrafiltration rate have an impact on the blood treatment unit simultaneously during at least one time period $\Delta t2$.

According to some embodiments, the method comprises controlling timing of the temporary change of the flow rate in the blood circuit and controlling timing of the temporary decreasing of the ultrafiltration rate such that the temporary decreasing of the ultrafiltration rate has an earlier impact on the blood treatment unit than the temporary change of the flow rate in the blood circuit has to the blood treatment unit.

According to some embodiments, the method comprises controlling timing of the temporary change of the flow rate in the blood circuit and controlling timing of the temporary decreasing of the ultrafiltration rate such that the temporary change of the flow rate in the blood circuit has an earlier impact on the blood treatment unit than the decreasing of the ultrafiltration rate has to the blood treatment unit.

According to some embodiments, the determined system parameter is based on one or several of a current $I_B$ consumed by a motor of the blood pump, a system pressure $P_{bi}$, a transmembrane pressure, TMP, across the blood treatment unit, an infusion flow rate $Q_{TR}$, a post-dilution flow rate $Q_{post}$, a haemoconcentration of the blood $C_E$, an ultrafiltration, UF, coefficient, a clearance K and/or another efficiency parameter of the treatment. The system parameter to be determined may also be determined based on a combination of any of the specified parameters.

According to a third aspect, the disclosure relates to a computer program at a system, wherein the computer program comprises computer instructions to cause a control unit to perform the method as explained herein.

According to a fourth aspect, the disclosure relates to a computer program product comprising computer instructions stored on a computer readable medium for performing the method as explained herein.

DETAILED DESCRIPTION

Figure 1:
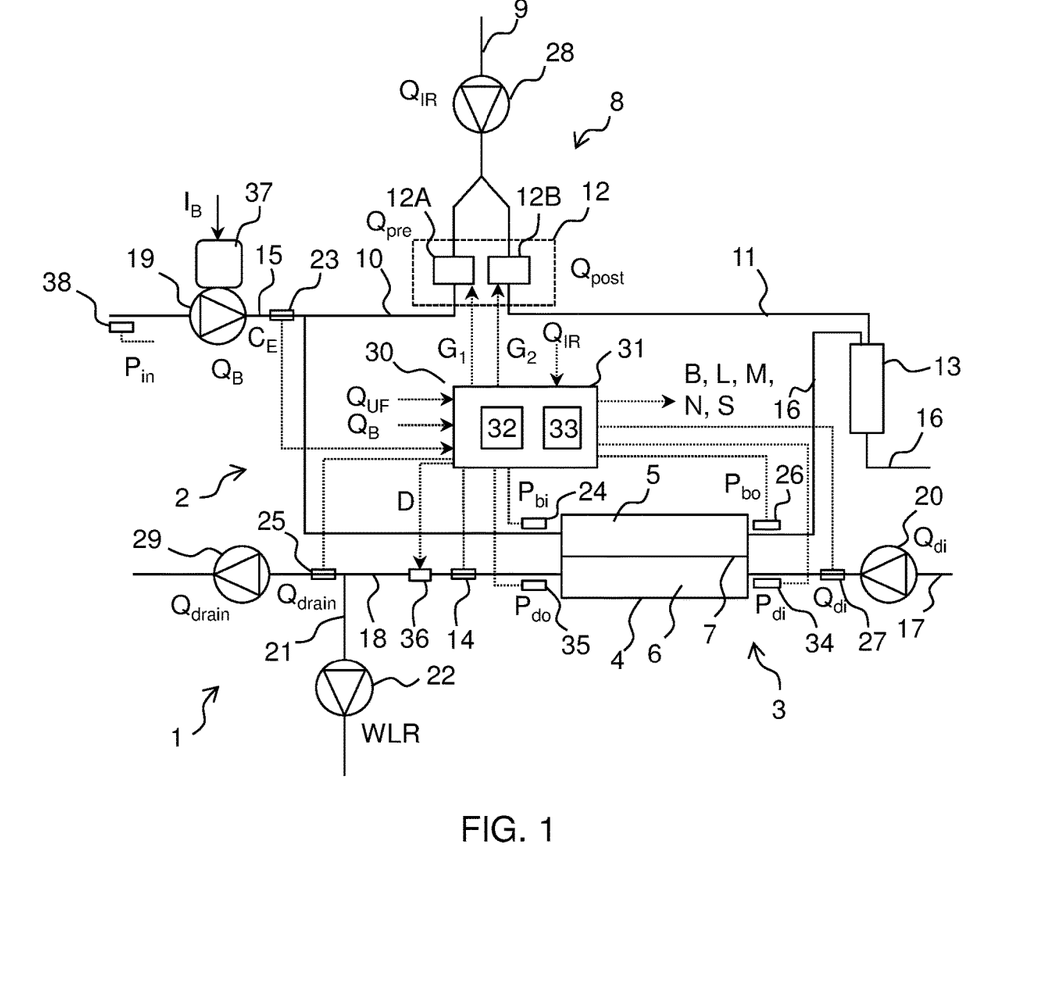
FIG. 1 illustrates a system for a renal replacement treatment according to one embodiment.

In FIG. 1 a renal replacement therapy system 1 is illustrated. The system 1 comprises an extracorporeal blood circuit 2, a dialysis fluid circuit 3 and a blood treatment unit 4. The blood treatment unit 4 may be a filter unit or a dialyzer. The blood treatment unit 4 comprises a blood compartment 5 and a fluid compartment 6 separated by a semipermeable membrane 7. The semipermeable membrane 7 may be made of a plurality of hollow fibers.

The extracorporeal blood circuit 2 comprises an arterial line 15 connected to an inlet of the blood compartment 5 of the blood treatment unit 4, and a venous line 16 connected to an outlet of the blood compartment 5 of the blood treatment unit 4. The blood treatment unit 4 is thus arranged connected to the blood circuit 2 for extracorporeal circulation of blood. The arterial line 15 is fitted with a blood pump 19 arranged to create a blood flow rate $Q_B$ in the arterial line 15. The blood pump 19 may be a peristaltic blood pump. The venous line 16 is fitted with a drip chamber 13. The arterial line 15 may be fitted with an auxiliary drip chamber (not shown) downstream the blood pump 19.

A motor 37 is arranged to rotate the blood pump 19. The motor 37 may be a brushed or brushless DC motor. A motor controller regulates the rotational speed of the blood pump 19. The speed of the blood pump 19, expressed as rotations per minute (RPM), regulates the blood flow rate $Q_B$ in the arterial line 15. The blood pump speed is dependent upon the voltage applied to the motor 37. Further, the blood flow rate $Q_B$ in the arterial line downstream the blood pump 19 is mainly proportional to the blood pump speed. This proportionality is based on the volumetric stroke volume of the blood pump that is virtually constant. However, smaller but sometimes significant deviations of the proportionality between the voltage and the flow exist due to long time use of the pump segment, the pressure $P_{in}$ to the pump, the pump current $I_B$ etc. However, different types of corrections means exist to account for such deviations and can be used if a better prediction of the exact blood flow rate is needed. Thus, the blood flow rate $Q_B$ may be derived from the blood pump speed.

The current $I_B$ consumed by the motor 37 is proportional to the pressure difference over the pump and if the arterial pressure $P_{in}$ is measured (or known to the system) the system pressure $P_{bi}$ can easily be calculated, as will be explained further below. The system pressure $P_{bi}$ may thus be derived from the current $I_B$.

The current $I_B$ consumed by the motor 37 may be measured directly with a built in sensor. The voltage may be measured with another built in sensor. The arterial pressure $P_{in}$ is measured with a pressure sensor 38 arranged to the arterial line 15 upstream the blood pump 19.

The dialysis fluid circuit 3 comprises a supply line 17 and a drain line 18. The supply line 17 is connected to an inlet of the fluid compartment 6 of the blood treatment unit 4, and the drain line 18 is connected to an outlet of the fluid compartment 6 of the blood treatment unit 4. The supply line 17 is fitted with a fresh dialysis fluid pump 20 arranged to create a fresh dialysis fluid flow rate $Q_{di}$ and the drain line 18 is fitted with a drain pump 29 arranged to create a used fluid flow rate $Q_{drain}$. In use, the upstream end of the supply line 17 is connected to a source of fresh dialysis fluid (not shown). The downstream end of the drain line 18 is connected to a container (not shown) for accumulation of the used dialysis fluid or to a sink (not shown).

A supplemental line 21 is in some embodiments connected to the drain line 18 between the blood treatment unit 4 and the drain pump 29, and fitted with an ultrafiltration pump 22 arranged to create a desired weight loss rate WLR. The ultrafiltration pump 22 is arranged to cause ultrafiltration of plasma water through the membrane 7 of the blood treatment unit 4. Instead of having two pumps 22, 29, a drain line 18 and a supplemental line 21, the flow rate $Q_{drain}$ of the drain pump 29 may be increased to also withdraw the WL amount (thus the WL rate). In operation of the drain pump 29, the flow rate $Q_{drain}$ of the drain pump 29 is then $Q_{di}$ plus the desired WLR. The ultrafiltration pump 22 and the supplemental line 21 are then not necessary.

The drain line 18 may be fitted with a drain flow restriction device 36 for controlling a fluid flow in the drain line 18. The drain flow restriction device 36 may be arranged downstream the blood treatment unit 4, but upstream any supplemental line 21. The drain flow restriction device 36 may be a valve set. The valve set may be an electromechanically actuated valve set.

An infusion line set 8 is in some embodiments connected to the extracorporeal blood circuit 2. The infusion line set 8 comprises a main line 9, which forks into a pre-dilution line 10 and/or a post-dilution line 11. In embodiments where a pre-dilution line 10 present, the pre-dilution line 10 is connected to the arterial line 15, e.g. downstream the blood pump 19, and upstream the blood treatment unit 4. In embodiments where a post-dilution-line 11 is present, the post-dilution line 11 is connected to the venous line 16, and here the post-dilution line 11 is connected to the venous drip chamber 13 in the venous line 16. The main line 9 is fitted with an infusion pump 28 creating an infusion flow rate $Q_{TR}$. A flow control means 12 is arranged to regulate a pre-dilution flow rate $Q_{pre}$ of substitution fluid in the pre-dilution line 10 and/or a post-dilution flow rate of substitution fluid in the post-dilution line 11. The flow control means 12 may comprise a first flow restriction device 12A arranged to the pre-dilution line 10, and/or a second flow restriction device 12B arranged to the post-dilution line 11. Alternatively, the flow control means 12 may comprise a common flow restriction device (not shown) fitted to the pre-dilution line 10 and the post-dilution line 11. In use, the upstream end of the main line 9 is connected to a source of substitution fluid (not shown). The pre-dilution line 10 is thus arranged for infusion of substitution fluid upstream the treatment unit 4. Further, the post-dilution line 11 is arranged for infusion of substitution fluid downstream the treatment unit 4.

The dialysis fluid and the substitution fluid may be the same kind of fluid, and may come from the same source. The fluids may be electrolyte and/or buffer solutions. The substitution fluid may also be referred to as infusion fluid or replacement fluid.

The renal replacement therapy system 1 further comprises a control circuit 30 comprising a control unit 31. The control unit 31 may comprise a processing unit 32 and a memory unit 33. The control unit 31 is configured to control the system 1 according to control instructions. Thus, the control unit is programmed to control the system 1 according to control instructions. The control circuit 30 comprises a sensor 24 arranged to the arterial line 15 directly upstream of the blood treatment unit 4 for supplying a signal $P_{bi}$ correlated to the blood pressure at the inlet of the blood treatment unit 4. The blood pressure in the arterial line 15, i.e. the outlet pressure from the blood pump 19, may alternatively be calculated as a function of the energy consumption of the blood pump 19 retrieved e.g. by measuring the power consumed by the motor 37 of the blood pump 19, see e.g. U.S. Pat. No. 6,585,675B1. Based e.g. on the current $I_B$ consumed by the motor 37, the torque produced by the motor 37 may be calculated if the speed and the physical parameters of the motor 37 is known. The torque consumed by the motor 37 is a function of the arterial pressure $P_{in}$ (the inlet pressure to the blood pump 19), the system pressure $P_{bi}$ and a torque needed to compress the pumps segment. The system pressure $P_{bi}$ may be expressed as $P_{bi} = (T_{motor} - T_{tube}) \cdot K_{conv} + P_{in}$, where $T_{motor}$ is the total torque output by the motor, $T_{tube}$ is the torque required to compress the pump segment (a constant of the system), and $K_{conv}$ is a conversion constant from torque to pressure for the system. As the $T_{tube}$ and $K_{conv}$, preferably compensated for usage time and temperature, are constant for the system the motor current $I_B$ may be used directly to indicate the blood pump output pressure, thus the system pressure $P_{bi}$, and thus any changes in the system pressure $P_{bi}$. The control circuit 30 further comprises a sensor 26 arranged to the venous line 16 downstream of the blood treatment unit 4 for supplying a signal $P_{bo}$ correlated to the blood pressure at the outlet of the blood treatment unit 4. The control circuit 30 further comprises a sensor 34 arranged to the supply line 17 for supplying a signal $P_{di}$ correlated to the dialysis fluid pressure at the inlet of the blood treatment unit 4. The control circuit 30 further comprises a sensor 35 arranged to the drain line 18 for supplying a signal $P_{do}$ correlated to the dialysis fluid pressure at the outlet of the blood treatment unit 4. The control circuit 30 further comprises a sensor 27 arranged to the supply line 17 for supplying a signal $Q_{di}$ correlated to the flow rate of the dialysis fluid at the inlet of the blood treatment unit 4. The control circuit 30 further comprises a sensor 25 arranged to the drain line 18 for supplying a signal $Q_{drain}$ correlated to the flow rate of the dialysis fluid at the outlet of the blood treatment unit 4 (and downstream any supplemental line 21). The control circuit 30 also comprises a haemoconcentration sensor 23 arranged somewhere along the arterial line 15, either upstream the connection of the pre-dilution line 10 to the arterial line 15, or downstream the connection of the pre-dilution line 10 to the arterial line 15. The haemoconcentration sensor 23 is arranged to generate a haemoconcentration signal $C_E$ correlated to the haemoconcentration of the blood in the arterial line 15 upstream the connection of the pre-dilution line 10 to the arterial line 15, or downstream the connection of the pre-dilution line 10 to the arterial line 15. It should be understood that the described system 1 is merely an example, and the system 1 may not comprise all of the above described sensors. However, the system 1 may alternatively comprise more and/or other than the described sensors.

Although not illustrated in the FIG. 1, the renal replacement therapy system 1 may comprise at least one system for preparation of the dialysis fluid and/or substitution fluid comprising arrangement for e.g. mixing the fluid or fluids. This may be referred to as on-line preparation of the dialysis fluid and/or substitution fluid. In the following disclosure, on-line preparation of the used fluids is assumed. The system may further comprise at least one heater arranged to heat the dialysis fluid and/or the substitution fluid and at least one degassing unit for degassing the dialysis fluid and/or the substitution fluid. The renal replacement therapy system 1 may also comprise various monitoring means comprising sensors, and optionally alarms, for detecting leakage anywhere in the system 1, for detecting abnormal behavior, for monitoring of various parameters such as conductivity, temperature, density, pH and other blood parameters, fluid parameters and/or system parameters.

One or several of the measured parameter values $P_{bi}$, $P_{bo}$, $P_{di}$, $P_{do}$, $Q_{di}$, $Q_{drain}$ and $C_E$ and the set values of various parameters, such as the blood flow rate $Q_B$, the flow rates $Q_{di}$ and $Q_{drain}$ of the drain pump 29 and the fresh dialysis fluid pump 20, the weight loss rate WLR, the ultrafiltration flow rate UFR across the membrane, and any infusion flow rate $Q_{IR}$, any pre-dilution flow rate $Q_{pre}$, any post-dilution flow rate $Q_{post}$ and any current $I_B$ are obtained e.g. received by the control unit 31 for controlling the system 1. The control unit 31 is configured to calculate e.g. the TMP, the clearance K, the UF coefficient, the UFR and other parameters based on the received parameters based on control instructions. The TMP may be expressed as a difference in pressure between the blood pressure in the blood compartment 5 and the fluid pressure in the fluid compartment 6. The TMP may thus be determined by calculating the difference between the blood pressure in the blood chamber 5 and the pressure in the fluid chamber 6. The blood pressure in the blood chamber 5 may be determined by $P_{bo}$ or $P_{bi}$, or an average of $P_{bi}$ and $P_{bo}$. The fluid pressure in the fluid chamber 6 may be determined by $P_{do}$ or $P_{di}$, or an average of $P_{do}$ or $P_{di}$. The TMP may be calculated as a difference between any of the $P_{bo}$, $P_{bi}$ or average of ($P_{bi}$ and $P_{bo}$), and any of the $P_{do}$, $P_{di}$ or average of ($P_{di}$ and $P_{do}$). For example, the TMP may be calculated as a difference between the post-filter pressures $P_{bo}$ and $P_{do}$. Alternatively the TMP is calculated as a difference between an average value of the blood pressure in the blood compartment 5 i.e. $P_{bi}$ and $P_{bo}$; and $P_{do}$ downstream the fluid compartment 6 (the post-filter fluid pressure). As a further alternative, the TMP is calculated as a difference between an average value of the blood pressure in the blood compartment 5 i.e. $P_{bi}$ and $P_{bo}$, and an average value of the fluid pressure in the fluid compartment 6, i.e. $P_{di}$ and $P_{do}$. In practice, the control unit 31 emits output signals for controlling the flow control means 12, e.g. the restriction devices 12A and 12B, the infusion pump 28, the fresh dialysis fluid pump 20, the drain pump 29, the ultrafiltration pump 22 and the blood pump 19, according to control instructions as will be made clear in the following description. For example, the control unit 31 may be configured to generate a control signal M for regulating the fresh dialysis fluid flow rate $Q_{di}$, and a control signal N for regulating the used fluid flow rate $Q_{drain}$. Further, the control unit 31 may be configured to generate a control signal S for regulating the flow rate WLR of fluid generated by the ultrafiltration pump 22. The control unit 31 may also be configured to generate a control signal B for regulating the blood flow rate $Q_B$.

The control unit 31 may further be configured to monitor one or several of the above described sensor values over time, and to calculate a change or changes of one or several of the parameters in Δ-values. For example: $\Delta P_{bi}$, $\Delta P_{bo}$, $\Delta P_{di}$, $\Delta P_{do}$, $\Delta Q_{di}$, $\Delta Q_{drain}$, $\Delta C_E$, $\Delta Q_B$, $\Delta Q_{di}$, $\Delta Q_{drain}$, $\Delta$WLR, $\Delta$UFR, $\Delta Q_{IR}$, $\Delta Q_{pre}$, $\Delta Q_{post}$, $\Delta I_B$, $\Delta$TMP, $\Delta$K, $\Delta$UF coefficient, $\Delta$UFR.

The first and second flow restriction devices 12A and 12B may be independently controlled. Thus, the first flow restriction device 12A arranged to the pre-dilution line 10 is arranged to regulate a flow $Q_{pre}$ in the pre-dilution line 10. The second flow restriction device 12B arranged to the post-dilution line 11 is arranged to regulate a flow rate $Q_{post}$ in the post-dilution line 11. The flow restriction devices 12A, 12B may be valve sets. The valve sets may be electromechanically actuated valve sets. One or both of the flow restriction devices 12A, 12B may instead be a pump or pumps (not shown) arranged to the pre-dilution line 10 and the post-dilution line 11, respectively.

In use, the flow rate of substitution fluid is regulated by adjusting the delivery, by the infusion pump 28, of the substitution fluid. The control unit 31 is configured to generate a control signal L to regulate the infusion flow rate $Q_{IR}$ of fluid generated by the infusion pump 28. The settings of the flow restriction devices 12A and 12B thereafter determines if the substitution fluid should be conducted in the pre-dilution line 10 or in the post-dilution line 11. The control unit 31 may be configured to generate a control signal $G_1$ to regulate the first flow restriction means 12A, and to generate a control signal $G_2$ to regulate the second flow restriction means 12B. According to one embodiment, the pre-dilution flow $Q_{pre}$ and the post-dilution flow $Q_{post}$ are never simultaneous flows. That is, if the first flow restriction device 12A allows a flow $Q_{pre}$, the second flow restriction device 12B stops the flow $Q_{post}$. And vice versa, if the second flow restriction device 12B allows a flow $Q_{post}$, the first flow restriction device 12A stops the flow $Q_{pre}$. Of course, both the first and the second flow restriction means may stop their flows $Q_{pre}$ and $Q_{post}$, respectively, to achieve no dilution at all. No dilution may also be achieved by controlling the infusion pump 28 to stop the infusion flow rate $Q_{IR}$. According to one embodiment, the control of the infusion pump 28 and the control of the flow control means 12 are synchronized. "Flow" is here used as a synonym to "flow rate".

The system 1 may be set in a plurality of different modes to automatically enable different kinds of treatments, for example hemofiltration (HF), hemodiafiltration (HDF), hemodialysis (HD) or ultrafiltration (UF). Because of the flow control means 12 and the infusion pump 28, it is possible to switch between post-dilution mode, pre-dilution mode, simultaneous post-dilution and pre-dilution mode, and also no-dilution mode, e.g. UF, without manual intervention, and also during treatment.

In case the system 1 has on-line preparation, the total ultrafiltration (UF) across the membrane 7 may be controlled in two ways by the ultrafiltration pump 22 (or the drain pump 29 if there is no separate ultrafiltration pump 22) and the infusion pump 28; in volume mode and in TMP mode. In both modes the difference between the flow rates $Q_{di}$+WLR and $Q_{drain}$ is used to control the ultrafiltration pump 22 and the drain pump 29 such that the difference agrees with the desired weight loss rate WLR. The WLR is set to zero if the ultrafiltration pump 22 and the fluid line 21 are not existent contrary to what is shown in the FIG. 1. In volume mode the infusion pump 28 is kept at a constant infusion flow rate $Q_{IR}$, and the TMP is allowed to vary. In TMP mode the desired TMP is maintained constant by controlling the infusion flow rate $Q_{IR}$ of the infusion pump 28 which will end up at a value such that UFR=WLR+$Q_{IR}$. This relation is thus maintained in both modes. The control unit 31 is configured to control the system 1 to either volume mode or TMP mode.

As soon as the blood treatment starts, the membrane 7 may start to clog caused by the membrane fouling. During the first couple of minutes, proteins in the blood are adsorbed or deposited on the surface of the membrane 7 and thus on the surface of the pores of the membrane 7, which leads to a change in membrane behavior. This phenomenon is here referred to as an initial clogging and is normally considered irreversible in nature. Some recent membranes are designed to take account for the initial clogging, such that they reach their nominal filtration properties after formation of the initial clogging.

As the treatment continues the secondary membrane of material is built up on the surface of the membrane 7 caused by the concentration polarization. This secondary membrane can be controlled by means of high shear on the membrane surface, if high shear can be tolerated in operation.

In order to reduce the membrane fouling, the control instructions comprise to, during a treatment, determine a value of a system parameter and to determine an indication of membrane fouling of the membrane 7 in the blood treatment unit 4 based on a predetermined criterion for the system parameter value. In response to such an indication, the control instructions comprise to activate an automatic anti-fouling measure comprising a temporary change of the flow rate in the blood circuit 2 upstream the blood treatment unit 4, and a temporary decrease of the ultrafiltration rate (UFR) across the semipermeable membrane 7, wherein timing of the temporary change of the flow rate in the blood circuit 2 and a timing of the temporary decrease of the UFR are synchronized. The automatic anti-fouling measure is performed automatically by the system 1, without any manual intervention. After the anti-fouling measure is finished, the system 1 returns automatically to normal operation with its previous set parameters, or may adapt its parameters to the anti-fouling measure made.

The system parameter to be determined may be based on one or several of a current $I_B$ consumed by a motor 37 of the blood pump 19 in order to provide a certain system pressure $P_{bi}$, the transmembrane pressure, TMP, across the blood treatment unit 4, the system pressure $P_{bi}$, the infusion flow rate $Q_{IR}$, the post-dilution flow rate $Q_{post}$, the pre-dilution flow rate $Q_{pre}$, the haemoconcentration of the blood $C_E$, an ultrafiltration (UF) coefficient, the ultrafiltration rate (UFR), the clearance K and/or another efficiency parameter of the treatment. The system parameter value may also be based on a change over time of one or several of the above described alternatives in Δ-values, e.g. $\Delta I_B$, $\Delta P_{bi}$, ΔTMP, $\Delta Q_{IR}$, $\Delta Q_{post}$, $\Delta Q_{pre}$, $\Delta C_E$, ΔUF coefficient, ΔK. As has been previously explained, these system parameter values may be sensor values received by the control unit 31, or system parameter values calculated by the control unit 30 by using known equations, constants and received sensor values. According to one embodiment, the predetermined criterion comprises a limit value of the system parameter value. The control instructions further comprises to compare the determined system parameter value with the limit value of the system parameter value, respectively, and to control the anti-fouling measure based on a result of the comparison. For example, the control instructions may comprise instructions to control activation and/or a length of the at least one time period Δt1 based on the result of the comparison. Examples of this kind of activation will be explained in the following with reference to FIGS. 2-4. The predetermined criterion may alternatively or also comprise a table. The table may comprise one or several relations between the system parameter value and anti-fouling measures, such that a certain system parameter value corresponds to one or several anti-fouling measures that should be done. The control instructions may thus comprise to look up the system parameter value in the table to find out if any anti-fouling measure should be done corresponding to the system parameter value.

Thus, each time a system parameter value is indicating membrane fouling, e.g., is equal to or goes beyond the limit value of the system parameter or indicates that an anti-fouling measure should be done, an automatic anti-fouling measure is activated. Alternatively it may be required that a plurality of different system parameter values are indicating membrane fouling, thus are equal to or goes beyond their respective limit value, in order for the automatic anti-fouling measure to be activated. According to a further alternative, the system parameter value is determined based on a combination or function of a plurality of the above described parameters.

The control instructions may comprise to maintain the automatic anti-fouling measure for a certain time period Δt1 after activation of the same, e.g. based on the result of the comparison or comparisons. The certain time-period Δt1 may have a length between about 0.1-6 seconds, and more preferably between 1-3 seconds.

According to some embodiments, the temporary change of the flow rate in the blood circuit 2 comprises to infuse a volume of substitution fluid via the pre-dilution line 10 to the blood circuit 2. The infusion of a volume of substitution fluid is accomplished by the flow control means 12. The control unit 31 is then configured to control the flow control means 12 to temporarily increase the pre-dilution flow rate $Q_{pre}$ of substitution fluid in the pre-dilution line 10, such that a predetermined volume of substitution fluid is added to the arterial line 15 via the pre-dilution line 10. The infused volume may be a pre-set amount of between 10-500 ml of substitution fluid, and more preferably between 20-100 ml. Alternatively, the infused volume may be set in relation to a volume of substitution fluid or flow rate of substitution fluid added via the post-dilution line 11. The temporary increase of the pre-dilution flow rate $Q_{pre}$ may then comprise an increase of the pre-dilution flow rate $Q_{pre}$ to between 60% and 400% of the current post-dilution flow rate $Q_{post}$, e.g. 80%, 100% or more. More specifically, the temporary increase of the pre-dilution flow rate $Q_{pre}$ may comprise an increase of the pre-dilution flow rate $Q_{pre}$ to more than 100% of the current post-dilution flow rate $Q_{post}$. For example, the pre-dilution flow rate $Q_{pre}$ may be 110%, 130%, 150%, 200%, 250%, 300%, 350% or 400% of the current post-dilution flow rate $Q_{post}$ during the time period $\Delta t1$. The pre-dilution flow rate may be increased from zero flow rate, thus, from no pre-dilution flow at all. Simultaneously, thus while the pre-dilution flow rate $Q_{pre}$ is increased, the control unit 31 may be configured to regulate the control means 12 such that the post-dilution flow rate $Q_{post}$ is lowered or set to zero. An increase of pre-dilution flow rate $Q_{pre}$, and if a post-dilution flow was present: a decrease of the post-dilution flow rate $Q_{post}$, during a limited time period, e.g. $\Delta t1$, is hereafter referred to as a "temporary flushing".

By temporarily increasing the pre-dilution flow rate, the shear force in the blood compartment 5 is then just temporarily raised, but enough to reduce or remove the secondary membrane build-up. The volume of pre-dilution fluid becomes limited and affects the composition of the blood only for a short period of time. The robustness of the treatment can thus be maintained, and as the secondary membrane decreases the efficiency, the efficiency of the treatment is enhanced.

According to some embodiments, the temporary change of the flow rate in the blood circuit 2 comprises to decrease or to stop the velocity of the blood pump 19. A decrease or stop of the blood flow reduces the amount of blood in the blood compartment 5, and thus also the pressure in the blood compartment 5. The secondary membrane build-up then more easily comes loose from the membrane 7. If at the same time the pressure in the fluid compartment 6 is increased such that a backwash is made, the removal of the secondary membrane is further facilitated as will be explained in the following. Alternatively, the temporary change of the flow rate in the blood circuit 2 comprises to increase the velocity of the blood pump 19. A temporary flushing by means of an increased blood flow may then be achieved.

Figure 2A:
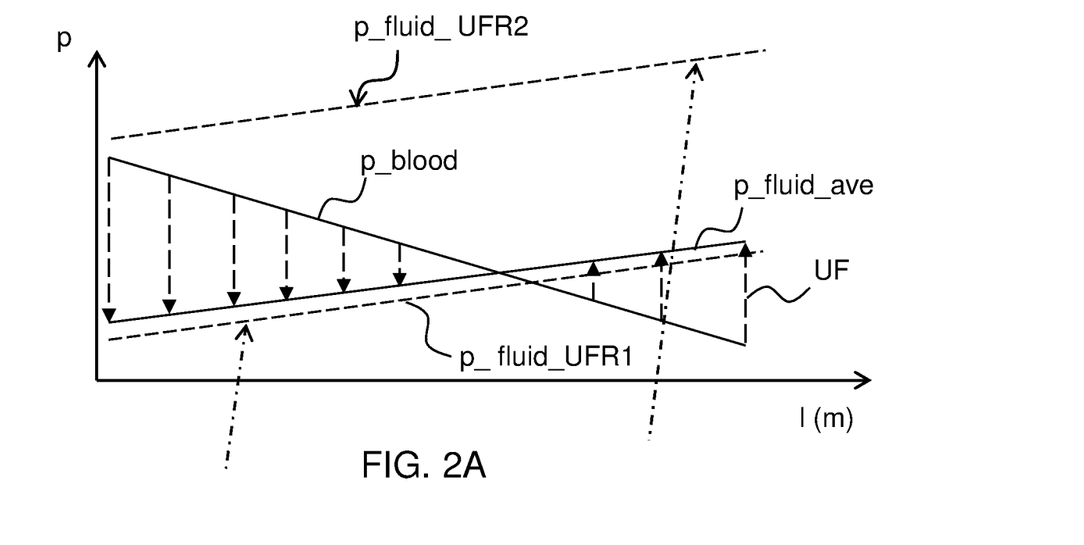
FIG. 2A illustrates the resulting ultrafiltration (UF) in the blood treatment unit across and along the semipermeable membrane.
Figure 2B:
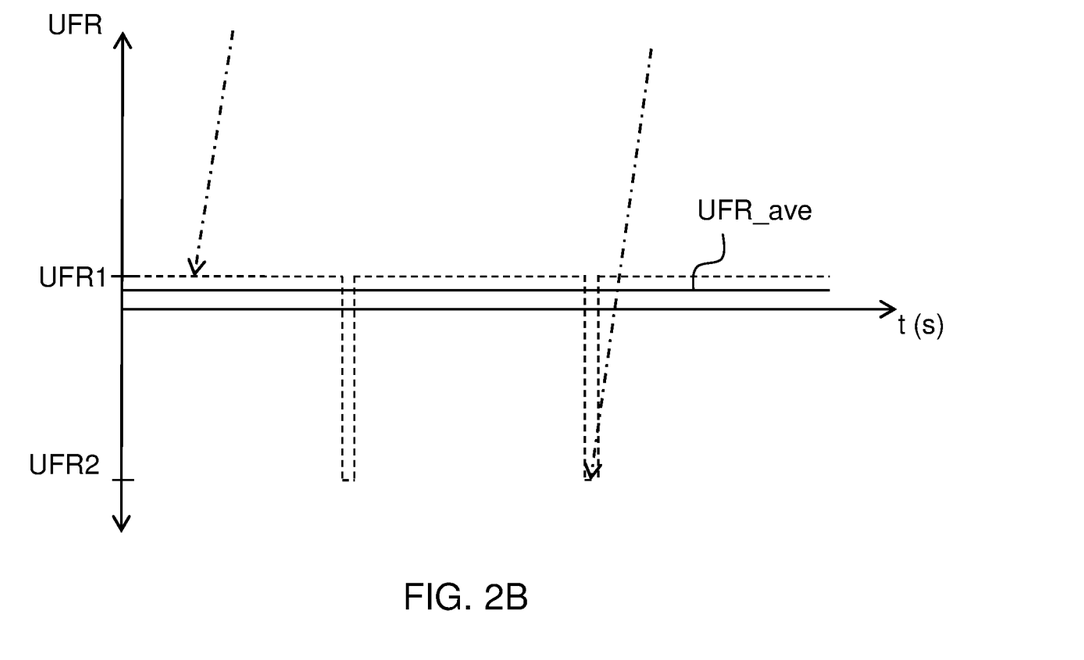
FIG. 2B illustrates an average UFR over time across the semipermeable membrane.

FIG. 2A illustrates the resulting ultrafiltration (UF) in the blood treatment unit 4 across the semipermeable membrane 7 in a diagram with pressure p on one axis and length 1 of the blood treatment unit, i.e. here the membrane 7, on the other axis. The solid line "p_blood" illustrates a schematic pressure drop in the blood compartment 5 from the blood inlet to the blood outlet thereof. The solid line "p_fluid_ave" illustrates a schematic pressure drop in the fluid compartment 6 from the fluid inlet to the fluid outlet thereof. Between the lines p_blood and p_fluid_ave the resulting UF across the membrane 7 is illustrated with dashed lines. The arrows on the dashed lines are illustrating the direction of the UF. As can be seen from the diagram and as known to the skilled person, the UF varies along the membrane 7 because of the pressure gradients from the pressure drops. FIG. 2B illustrates an average UFR (illustrated with the solid line UFR_ave) across the membrane 7 along the X-axis in FIG. 2A, during a time t illustrated by the X-axis in this FIG. 2B. The UFR is illustrated by the Y-axis in FIG. 2B. It is here assumed that the blood pressure in the blood compartment 5 has a constant gradient, in the solid line UFR_ave. To illustrate how the pressure gradient in the fluid compartment 6 varies with a varying UFR (dashed lines in both FIGS. 2A and 2B), the UFR is decreased from a desired positive UFR1 where plasma is withdrawn from the blood compartment 5 through the membrane 7 and into the fluid compartment 6, to a negative UFR2 where dialysis fluid is infused from the fluid compartment 6 through the membrane 7 and into the blood compartment 5 to thereby create a backwash (as will be explained in the following). The resulting pressure in the fluid compartment 6 over the length of the membrane 7 when the UFR is UFR1 is illustrated in FIG. 2A by the dashed line p_fluid_UFR1. The resulting pressure over the length of the membrane 7 when the UFR is UFR2 is illustrated in FIG. 2A by the dashed line p_fluid_UFR2. In FIG. 2B the netto or average UFR over time is illustrated with the line UFR_ave. Two semi-dotted lines between FIGS. 2A and 2B are illustrating that the pressure p_flud_UFR1 (of FIG. 2A) is related to UFR1 (of FIG. 2B), and the pressure p_fluid_UFR2 (of FIG. 2A) is related to UFR2 (of FIG. 2B).

During normal treatment, the pressure in the fluid compartment 6 is generally lower than the pressure in the blood compartment 5, to withdraw excess fluid from the patient. A temporary decrease of the ultrafiltration rate across the semipermeable membrane 7 has the effect that the negative pressure in the fluid compartment 6 of the blood treatment unit 4 becomes reduced, equalized or even reversed, compared to the pressure in the fluid compartment 6 during normal treatment. To reduce the negative pressure in the fluid compartment 6, in relation to the blood pressure in the blood compartment 5, here means to reduce the pressure difference between the blood compartment 5 and the fluid compartment 6 eventually up to the point where the pressure is higher in the fluid compartment 6 compared to the blood compartment 5. With reference to FIG. 2A, this may correspond to raising the pressure in the fluid compartment 6 from the pressure p_fluid_UFR1 (where a positive UFR1, see FIG. 2B, is withdrawn) up to the pressure p_fluid_UFR2 (where a negative UFR2 is withdrawn, see FIG. 2B, thus, fluid is pushed into the blood compartment 6 from the fluid compartment 5). These modes, i.e. reduction, equalization or reversing the negative pressure in the fluid compartment 6, may be accomplished by regulating the dialysis fluid flow rate in the supply line 17 and/or the used fluid flow rate $Q_{drain}$ in the drain line 18 and/or the WLR in the supplemental line 21. For example, in a HF or HDF-treatment, the control instructions may comprise to temporarily stop the WLR in the supplemental line 21 (assuming the same flow rates $Q_{drain}$ and $Q_{di}$ in HDF). Thereby the pressure in the fluid compartment 6 will increase and the secondary membrane build-up on the membrane 7 in the blood compartment 5 will easier become loose from the membrane 7.

Alternatively, the used fluid flow rate $Q_{drain}$ may be reduced or stopped by controlling the drain pump 29 towards or to zero flow rate, in addition to stopping the WLR. The pressure in the fluid compartment 6 will then gradually become less negative (compared to the pressure in the blood compartment 5) as the fresh dialysis fluid pump 20 is still supplying dialysis fluid to the fluid compartment 6. After a short while the pressures in the blood treatment unit 4 will be equalized, thus, the pressure in the fluid compartment 6 will be the same as the pressure in the blood compartment 5. However, as there is still a blood flow in the blood compartment 5, there will be a pressure gradient along the membrane 7. After a further while, the pressure in the fluid compartment 6 becomes greater than the pressure in the blood compartment 5, and dialysis fluid starts to go through the membrane 7 to the blood compartment 5 and thereby pushes the secondary membrane build-up, and any eventual particles trapped in the pores, into the blood compartment 5. The pushed particles and aggregates of particles may then be flushed away by an increased fluid flow rate in the blood compartment 5. A filter in the venous drip chamber 13 collects any eventual aggregates that are considered too large to be maintained in the blood before the blood is being returned to the patient.

When the pressure in the fluid compartment 6 becomes positively greater than the pressure in the blood compartment 5, the dialysis fluid is pushed into the blood compartment 5. This corresponds to a negative UFR. A controlled infusion of dialysis fluid from the fluid compartment 6, through the membrane 7 and into the blood compartment 5 is here referred to as a backwash of the membrane 7. The temporary decrease of the ultrafiltration rate across the semipermeable membrane 7 may cause such a backwash and thus comprise to infuse a controlled volume of dialysis fluid from the fluid compartment 6 into the blood compartment 5 through the semipermeable membrane 7. The controlled infusion of dialysis fluid may thus be accomplished by controlling the pressure in the fluid compartment compared to the pressure in the blood compartment 5, such that the pressure in the fluid compartment is positively increased and becomes greater than the pressure in the blood compartment 5. In other words, the UFR across the membrane 7 is controlled. This is exemplified in FIGS. 2A and 2B, wherein the UFR is decreased to UFR2 whereby the pressure in the fluid compartment 6 increases as illustrated by p_fluid_UFR2 such that it is greater than the pressure in the blood compartment 5, p_blood. The pressure increase may be accomplished by controlling any of the fresh dialysis fluid pump 20, ultrafiltration pump 22 and/or drain pump 29. For example, as previously explained, the drain pump 29 and the ultrafiltration pump 22 may be controlled to decrease or stop their flow rates $Q_{drain}$ and WLR, respectively, in order to positively increase the pressure in the fluid compartment 6. Alternatively or as a complement, the fresh dialysis fluid pump 20 may be controlled to increase the fresh dialysis fluid flow rate $Q_{di}$ in order to positively increase the pressure in the fluid compartment 6. Alternatively, the pressure increase may be accomplished by controlling one or several valves arranged to regulate the flow rate in the drain line 18, e.g. the flow restriction device 36, and/or the flow rate in the supplemental line 21. The controlled volume of dialysis fluid infused during backwash is according to some examples between 1-40 ml, and more preferably between 2-10 ml. The time period Δt1 this volume is infused is between 0.1-6 seconds, and more preferable between 1-3 seconds. If the controlled volume is zero, then there is no backwash, however the negative pressure acting on the secondary membrane from the fluid compartment 6 will decrease and may become zero such that the secondary membrane easier comes loose from the real membrane 7. The backwash may be performed as one continuous separate infusion e.g. during the time period Δt1.

In all the above described alternatives, a decrease of the positive UFR across the semipermeable membrane 7 is accomplished, thus, less fluid is drawn from the blood. This may be achieved by a reduction of the flow rate in the dialysis fluid circuit 3 downstream the blood treatment unit 4. The temporary decrease of the UFR across the semipermeable membrane 7 may comprise to make the pressure in the fluid compartment 6 less negative than before the temporary decrease, for example to equalize the average pressure in the fluid compartment 6 and the pressure in the blood compartment 5. The UFR is then zero (according to FIG. 2B), thus, the net result is that no fluid is drawn from the blood compartment 5 and no fluid is pushed into the blood compartment 5. The temporary decrease of the ultrafiltration rate across the semipermeable membrane 7 is thus adapted to cause the ultrafiltration rate to be zero.

According to some embodiments, the control instructions comprise to control the timing of the temporary change of the flow rate in the blood circuit 2 and to control the timing of the temporary decrease of ultrafiltration rate in the dialysis fluid circuit 3 such that the temporary change in the flow rate in the blood circuit 2 and the temporary decrease of ultrafiltration rate have an impact on the blood treatment unit 4 simultaneously, e.g. during at least one time period Δt2 within the time period Δt1. The control instructions may take into account any compliance of the system, e.g. derived from the drip chamber 13 or the blood treatment unit 4. Because of compliance it may take some time before a change of a flow rate has an impact on the system. The control instructions will then take this time into account.

The control instructions may for example comprise to control the timing of the temporary change of the flow rate in the blood circuit 2 and to control the timing of the temporary decrease of ultrafiltration rate, such that the temporary decrease of the ultrafiltration rate has an earlier impact on the blood treatment unit 4 than the impact the temporary change of the flow rate in the blood circuit 2 has to the blood treatment unit 4. By knowing the predetermined time-lengths, the control unit 31 can easily calculate when the different pumps 19, 20, 22, 28, 29 should be regulated in order to make the temporary decrease of the ultrafiltration rate to have an earlier impact on the blood treatment unit 4 than the impact the temporary change of the flow rate in the blood circuit 2 has to the blood treatment unit 4. If the decrease of the ultrafiltration rate has an impact on the blood treatment unit 4 earlier than the temporary change of the flow rate in the blood circuit 2, the negative pressure from the fluid compartment 6 that acts upon the secondary membrane to hold it against the membrane 7 will be less negative, zero or reversed before the fluid or fluid rate in the blood compartment 5 is changed. The secondary membrane will then already be slightly more loose or even pushed away from the membrane 7 when the temporary change of the flow rate in the blood circuit 2 has its impact on the blood treatment unit 4, whereby the secondary membrane more easily is flushed away with e.g. the infused volume of substitution fluid via the pre-dilution line 10 or increased flow rate of the blood pump 19.

Alternatively, the control instructions comprise to control the timing of the temporary change of the flow rate in the blood circuit 2 and to control the timing of the temporary decrease of the ultrafiltration rate, such that the temporary change of the flow rate in the blood circuit 2 has an earlier impact on the blood treatment unit 4 than the impact of the temporary decrease of the ultrafiltration rate has to the blood treatment unit 4. By knowing the predetermined time-lengths as have been previously explained, the control unit 31 can easily calculate when the different pumps 19, 20, 22, 28, 29 should be regulated in order to make the temporary reduction of the flow rate in blood circuit 2 to have an earlier impact on the blood treatment unit 4 than the impact the temporary decrease of the ultrafiltration rate has to the blood treatment unit 4. Just before, e.g. a few seconds before, an infusion of dialysis fluid during a backwash is performed the blood pump 19 may be stopped. Thereby the pressure gradient existing in the blood compartment 5 during normal blood flow rate through the blood compartment 5 is equalized. The hereafter conducted backwash will then be approximately equal in all segments of the blood treatment unit 4. As the pressure from pumped blood in the blood compartment 5 to the membrane 7 then is removed, the effect of the backwash may be enhanced. The blood pump 19 may be stopped for a predetermined time length, e.g. the same time length as the time length of the decrease of the dialysis fluid rate, e.g. the at least one time period Δt1. Instead of stopping the blood pump 19, the speed of the blood pump 19 may be reduced. The pressure gradient in the blood compartment 5 will then not be equalized, but the pressure on the membrane 7 from the pumped blood is reduced and the effect of the backwash may be enhanced. After the time period Δt1, the blood pump 19 is resumed to normal operation.

The above described alternatives to control the timing of the temporary change of the flow rate in the blood circuit 2 and to control the timing of the temporary decrease of the ultrafiltration rate may also be combined. For example may an anti-fouling measure comprise to reduce or stop the velocity of the blood pump 19, to infuse a volume of substitution fluid via the pre-dilution line 10 and to perform a backwash; where these actions are synchronized in time such that first the reduction or stop of the velocity of the blood pump 19 starts to have an effect to the blood treatment unit 4, thereafter and secondly the backwash starts to have an effect to the blood treatment unit 4, and still thereafter and thirdly the infusion of the volume of substitution fluid starts to have an effect to the blood treatment unit 4.

The mentioned stopping of the blood pump 19 may be performed during the same time period or time periods Δt1, such that the blood flow is stopped during the time period or time periods Δt1. Alternatively, the blood pump 19 may be stopped during a same time length as Δt1, but be controlled to be stopped before the volume of substitution fluid is infused. As the pre-dilution flow rate $Q_{pre}$ is infused downstream the blood pump 19, a stop of the blood pump 19 will not influence the pre-dilution flow rate $Q_{pre}$. The fluid in the blood compartment 5 will however become very clean, that is, comprise almost only the substitution fluid infused, which may increase the effect of the anti-fouling measure. Instead of stopping the blood pump 19, the speed of the blood pump 19 may be reduced. The blood flow rate through the blood compartment 5 will then be reduced and the fluid comprises less blood particles than with normal blood flow rate, which may increase the effect of the anti-fouling measure. The control unit 31 may be configured to control the speed of the blood pump 19 accordingly, e.g. to reduce the speed of the blood pump 19 or stop the blood pump 19 as described in the foregoing.

According to one embodiment, the infusion or infusions of the backwash are only performed during the same time period or time periods Δt1 as the flow rate in the blood circuit 2 is changed. The stopping or reduction of the used fluid flow rate $Q_{drain}$ and/or the WLR may also be performed only during the same period of time Δt1. Thus, the decrease of the ultrafiltration rate may be performed only during the same period of time Δt1.

After the automatic anti-fouling measure and outside the time-period Δt1, the flow rates $Q_{di}$, $Q_{drain}$, WLR (if any), $Q_B$, $Q_{IR}$, $Q_{pre}$ and $Q_{post}$ may be resumed to normal operation. However, the total ultrafiltration rate UFR may be automatically increased and/or the post-dilution flow rate $Q_{post}$, if any, may be automatically decreased to compensate for the extra volumes infused to the blood during the anti-fouling measure. For each treatment, a desired UF-volume is determined that should be withdrawn from the patient during the treatment. The actually withdrawn UF-volume is continuously monitored by the system 1, also during the anti-fouling measure. The temporary decrease of the UFR caused by the anti-fouling measure is therefore known and can be compensated for during the remaining treatment. In other words, the control instructions may comprise to control the ultrafiltration rate after an anti-fouling measure, such that the temporary decrease of the ultrafiltration rate across the semipermeable membrane 7 is compensated for during the remaining treatment. Also, the control instructions may comprise to control the post-dilution rate after an anti-fouling measure, such that the temporary decrease of the post-dilution flow rate is compensated for during the remaining treatment.

Figure 3:
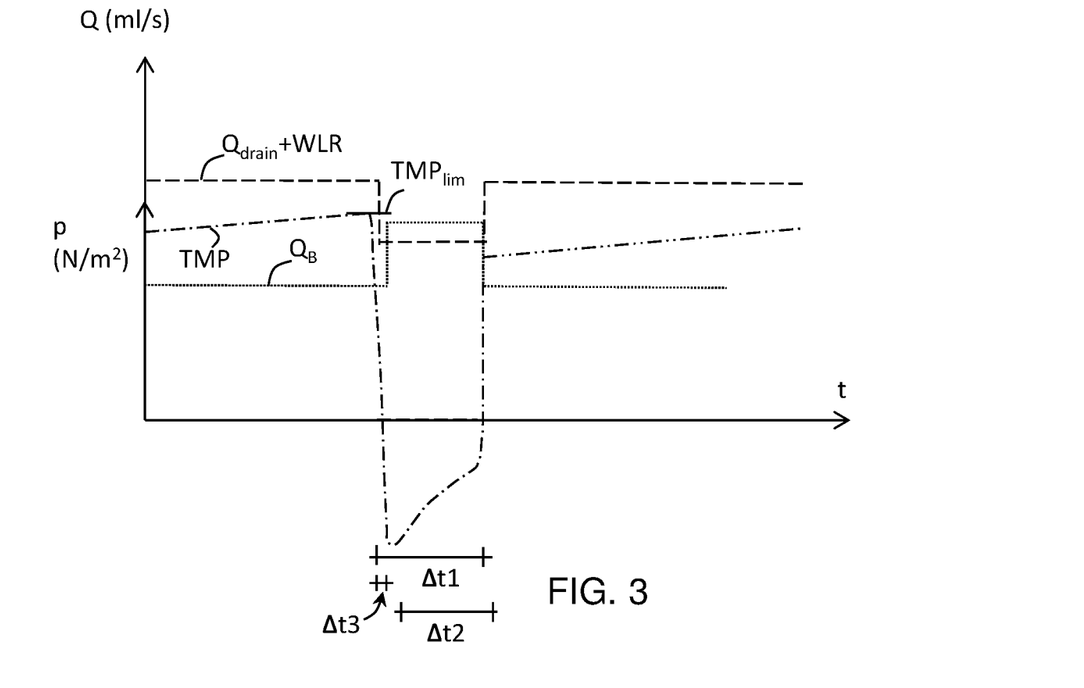
FIG. 3 shows a diagram illustrating anti-fouling measures of the membrane according to one embodiment.

In FIG. 3 one treatment example is illustrated in a first diagram of operating the system 1 where the anti-fouling measure is controlled in dependence of the system parameter TMP in volume mode. The first diagram has flow rate Q on its Y-axis, and time t on its X-axis. A diagram of the TMP of the blood treatment unit 4 is overlaid the first diagram, and has pressure p on its Y-axis and time t on its X-axis. As can be seen from the first diagram, the treatment is in HD with no substitution fluid. The blood flow rate $Q_B$ has a constant rate and the $Q_{drain}$ and WLR are together on a constant rate. As the membrane fouling adds on, the TMP increases. When the TMP is equal to or becomes greater than a predetermined upper $TMP_{lim}$-value, the anti-fouling measure is activated by reducing the $Q_{drain}$ and WLR (in FIG. 3. to zero). The activation of the anti-fouling measure also comprises activating a timer (software-implemented) and the start of the time period Δt1. The negative pressure difference between the pressure in the fluid compartment 6 and the pressure in the blood compartment 5 is then reduced, becomes zero and gradually the pressure difference becomes positive meaning that a backwash is performed and dialysis fluid is pushed from the fluid compartment 6 into the blood compartment 5. For example, the average pressure in the fluid compartment 6 may start from p_fluid_UFR1 (FIG. 2A) and when a backwash is performed the pressure may rise to p_fluid_UFR2 (FIG. 2B). Shortly after the anti-fouling measure is activated, after a time period Δt3, the blood flow rate $Q_B$ is increased in order to create a flushing of the membrane 7. The negative pressure in the fluid compartment 6 is here reduced earlier than the blood flow increase reaches the blood treatment unit 4, such that the secondary membrane becomes less bound to the membrane 7 than before and can be flushed away with the increased blood flow in the blood compartment 5. The decrease of the ultrafiltration rate and the increase of the blood flow rate $Q_B$ have a simultaneous effect on the blood treatment unit 4 during the time period Δt2. As shown in the diagram in FIG. 3, the time period Δt2 starts some time after both the rate changes have been made and thus both have an impact on the blood treatment unit 4. Because of the effects of the anti-fouling measure, the TMP decreases to a lower value than the $TMP_{lim}$-value. After the time period Δt1 the blood flow rate $Q_B$ resumes its normal flow rate. The TMP with time gradually increases again, and may again go beyond the $TMP_{lim}$-value. The same procedure is then repeated while the treatment is on-going. The system parameter is here thus the TMP.

Figure 4:
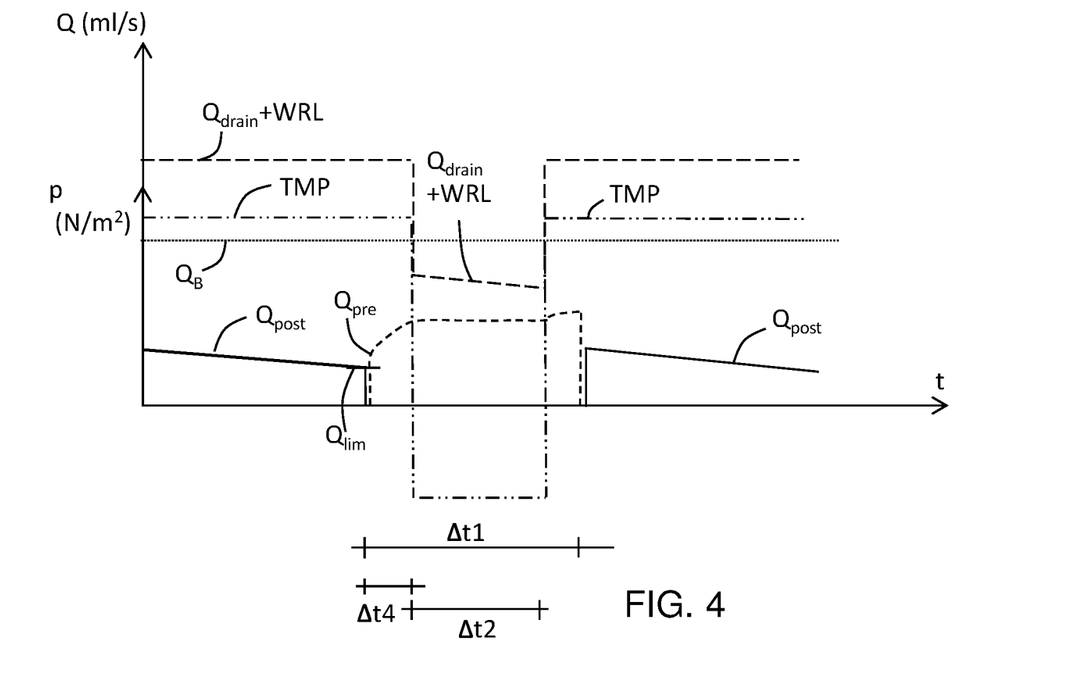
FIG. 4 shows a diagram illustrating anti-fouling measures of the membrane according to another embodiment.

In FIG. 4 another treatment example is illustrated in a second diagram, when operating the system 1 in TMP mode and the anti-fouling measure is controlled in dependence of $Q_{post}$. The second diagram has flow rate Q on its Y-axis, and time t on its X-axis. A diagram of the TMP of the blood treatment unit 4 is overlaid the second diagram, and has pressure p on its Y-axis and time t on its X-axis. As can be seen from the second diagram, the illustrated treatment is HDF in post-dilution mode with a varying flow rate $Q_{post}$ of substitution fluid added downstream the blood treatment unit 4 and no substitution fluid added upstream the blood treatment unit 4 from the start. The $Q_{post}$ is regulated such that TMP is held constant. Also the UFR is held constant, and $Q_{drain}$ and/or WLR are adjusted to accomplish a desired WLR. As the membrane fouling adds on, the UFR is decreased in order to accomplish a constant TMP whereby the post-dilution flow rate $Q_{post}$ is decreased. When the post-dilution flow rate $Q_{post}$ reaches or becomes lower than a predetermined lower flow rate $Q_{lim}$, the anti-fouling measure is activated by switching from post-dilution to pre-dilution. This is accomplished by decreasing the post-dilution fluid rate $Q_{post}$, e.g. to zero, and increasing the pre-dilution fluid flow rate $Q_{pre}$, e.g. to 100-400% of the previous post-dilution fluid flow rate $Q_{post}$. The decrease of the post-dilution fluid rate $Q_{post}$ may be started approximately simultaneously as the pre-dilution fluid flow rate $Q_{pre}$ is increased, thus when a first part of the anti-fouling measure is activated. The activation of the anti-fouling measure also comprises activating a timer (software-implemented) and the start of the time period Δt1. The increased flow rate $Q_{pre}$ dilutes the blood in the blood chamber 5 and intends to at least partially flush away the secondary membrane. The control parameter of the anti-fouling measure is now $Q_{pre}$. A time period Δt4 after the time period Δt1 has started, and while the pre-dilution flow rate $Q_{pre}$ is maintained (held constant), a backwash is created to push the secondary membrane away from the semipermeable membrane 7, or at least makes it less bound to the membrane 7 than before, such that the secondary membrane more easily can be flushed away with the increased flow rate in the blood compartment 5. Optionally, the backwash is started at the same time as the post-dilution is switched to pre-dilution. The fluid in the blood compartment 5 also contains less blood particles than before, because of the added pre-dilution flow, which facilitates the removal of the secondary membrane. The backwash is created by changing to an alternative TMP control during the time period Δt2. The alternative TMP control comprises decreasing the desired WLR by decreasing the $Q_{drain}$+WLR (optionally only $Q_{drain}$) to a lower value than before, e.g. 40% lower than before the decrease. The TMP will then decrease to a negative value while the $Q_{pre}$ is held constant. It is now desired to keep the TMP constant on the negative value, and the flow rate $Q_{drain}$+WLR (optionally only $Q_{drain}$) is allowed to vary. Because of the decreased $Q_{drain}$+WLR (optionally only $Q_{drain}$) and constant $Q_{pre}$, fluid from the dialysis chamber 6 is pushed into the blood chamber 5 through the semipermeable membrane 7. During the backwash, the control parameter of the anti-fouling measure is the flow rate $Q_{drain}$+WLR. The backwash is maintained for a time period Δt2. As the negative TMP should be maintained constant and the secondary membrane 7 gradually becomes cleaner and more permeable, the $Q_{drain}$+WLR is gradually further controlled (here decreased) to maintain the constant negative TMP. After the time period Δt2, the backwash is stopped by returning the control from this alternative TMP mode to normal TMP mode, and thereby controlling the TMP (by regulating $Q_{pre}$) to the previously set value before the anti-fouling measure was started, and controlling the $Q_{drain}$+WLR to the previously set value before the anti-fouling measure was started. The dilution is here still pre-dilution. The pre-dilution flow will now increase slightly, as the semipermeable membrane is more permeable than before. At the end of the time-period Δt1, the dilution flow is switched from pre-dilution to post-dilution. The pre-dilution flow rate is thus set to zero, and the post-dilution flow rate is controlled to achieve the desired TMP giving a desired WLR while maintaining the relationship UFR=WLR+$Q_{IR}$. Optionally, the switch from pre-dilution to post-dilution can be made at the same time as the returning the control from the alternative TMP mode to normal TMP mode, thus at the end of the time-period Δt2. Because it is now easier to withdraw fluid through the reduced secondary membrane 7, the desired TMP will enable a higher UFR. As the WLR is the same, the $Q_{IR}$, which is now $Q_{post}$, is raised in comparison with $Q_{lim}$.

Hence, during the backwash and thus the time period Δt2, the ultrafiltration rate across the semipermeable membrane 7 is decreased. Further, the flow rate in the blood circuit 2 is changed compared to the previous flow rate in the blood circuit 2 before the anti-fouling measure. The timing of the temporary change of the flow rate in the blood circuit 2 and the timing of the temporary decrease of the ultrafiltration rate are synchronized, as the backwash is started a time period Δt4 after the change of $Q_{post}$ and $Q_{pre}$, and the backwash is performed while there is a pre-dilution flow rate $Q_{pre}$. The time period for the whole anti-fouling measure is Δt1, and the backwash and the changes of flow rates $Q_{post}$ and $Q_{pre}$ are performed within this time period. The decrease of the ultrafiltration rate and the increase of the pre-dilution flow rate $Q_{pre}$ have a simultaneous effect on the blood treatment unit 4 at least during the time period Δt2. After the time period Δt2 the UFR across the membrane is increased. After the time period Δt1, the $Q_{post}$ gradually decreases again, and may again go beyond the $Q_{lim}$-value. The same procedure is then repeated while the treatment is on-going. Because of the flushing effect, the UFR will be increased in order to maintain a constant TMP.

Although the example in FIG. 4 was mainly performed in TMP mode, the same effects can be achieved in volume mode.

Thus, the set point for the TMP may be decreased during the time-period Δt2 of the anti-fouling measure as illustrated in FIG. 4. After the time-period of the anti-fouling measure, the set point for the TMP is changed back to the normal, previous value. The pressure over the membrane 7 in the treatment unit 4 will then decrease during the time-period of the anti-fouling measure, whereby the flushing becomes more efficient as the secondary membrane build-up on the membrane 7 will easier come loose from the membrane 7.

Further, the anti-fouling measure may be activated in response to an ultrafiltration flow rate UFR that is lower than a certain lower ultrafiltration flow rate limit UFR_lim. The anti-fouling measure may also be activated in response to a haemoconcentration value $C_E$ higher than a certain haemoconcentration limit value $C_{E\_lim}$.

According to a further embodiment, the anti-fouling measure may be activated in response to a certain efficiency of the treatment, as determined e.g. in EP1729836B1. An efficiency parameter of the treatment may be determined by calculating the UF coefficient as follows:

$$UF \text{ coefficient} = \frac{UFR}{TMP} \qquad (1)$$

The anti-fouling measure may then be activated in response to a UF coefficient lower than a certain UF coefficient limit value $UF_{coeff\_lim}$. Alternatively, an efficiency parameter may be determined by measuring the clearance K of the treatment, i.e. blood water clearance as described in U.S. Pat. No. 7,435,235B2 which content is hereby incorporated by reference. In HF clearance K may be calculated from a blood water flow rate $Q_{BW}$ the pre-dilution flow rate $Q_{pre}$, the post-dilution flow rate $Q_{post}$ and a desired weight loss rate WLR of the patient as follows:

$$K = \frac{Q_{BW}}{Q_{BW} + Q_{pre}} (Q_{pre} + Q_{post} + WLR) \quad (2)$$

The blood water flow rate $Q_{BW}$ is an estimate of the rate of the water in the blood, and is estimated with a factor $f_{BW}$~0.85-0.9 multiplied with the blood flow rate $Q_B$. Alternatively, the blood flow rate $Q_B$ may be used instead of the blood water flow rate $Q_{BW}$ as an approximation. To calculate the clearance K, the $Q_{BW}$ is then exchanged for $Q_B$ in equation (2). The clearance K may be compared to a limit value of the clearance parameter, and if the clearance K is lower than the limit value, the anti-fouling measure is activated during the time period $\Delta t1$.

The efficiency parameter may instead be the conductivity of the fluid in the drain line 18, or the concentration of at least one substance contained in the fluid in the drain line 18. The system 1 of FIG. 1 is then arranged with a sensor 14 for sensing such a fluid parameter, i.e. conductivity or concentration. The fluid parameter may then be compared to a limit value of the fluid parameter, and if the fluid parameter is equal to or goes beyond the limit value, i.e. is greater than the limit value or less than the limit value, respectively, depending on which parameter that is used, the anti-fouling measure may be activated during the time period $\Delta t1$.

The disclosure also relates to a method to be used in a renal replacement therapy system. The method may be performed with the system 1 illustrated in FIG. 1. The system 1 may be arranged for any or all of UF (Ultrafiltration), HD (Hemodialysis), HF (Hemofiltration) or HDF (Hemodiafiltration) treatment. The system 1 may also be arranged for all the treatments, and the control unit 31 in the system 1 will in dependence on input to the system 1 control the system 1 to perform a certain kind of treatment related to the input. A computer program P is loaded into the memory unit 33 of the control unit 31, and the computer program P comprises computer instructions, with other words control instructions, to cause the control unit 31 to perform the method according to any of the method steps as disclosed herein, when the computer program P is run on the processing unit 32. The processing unit 32 may comprise one or several central processing units (CPUs). The computer program P may reside on a computer program product, e.g. a memory unit in a computer or on a server, on a CD-rom, on a memory-stick or similar computer readable mediums.

Figure 5:
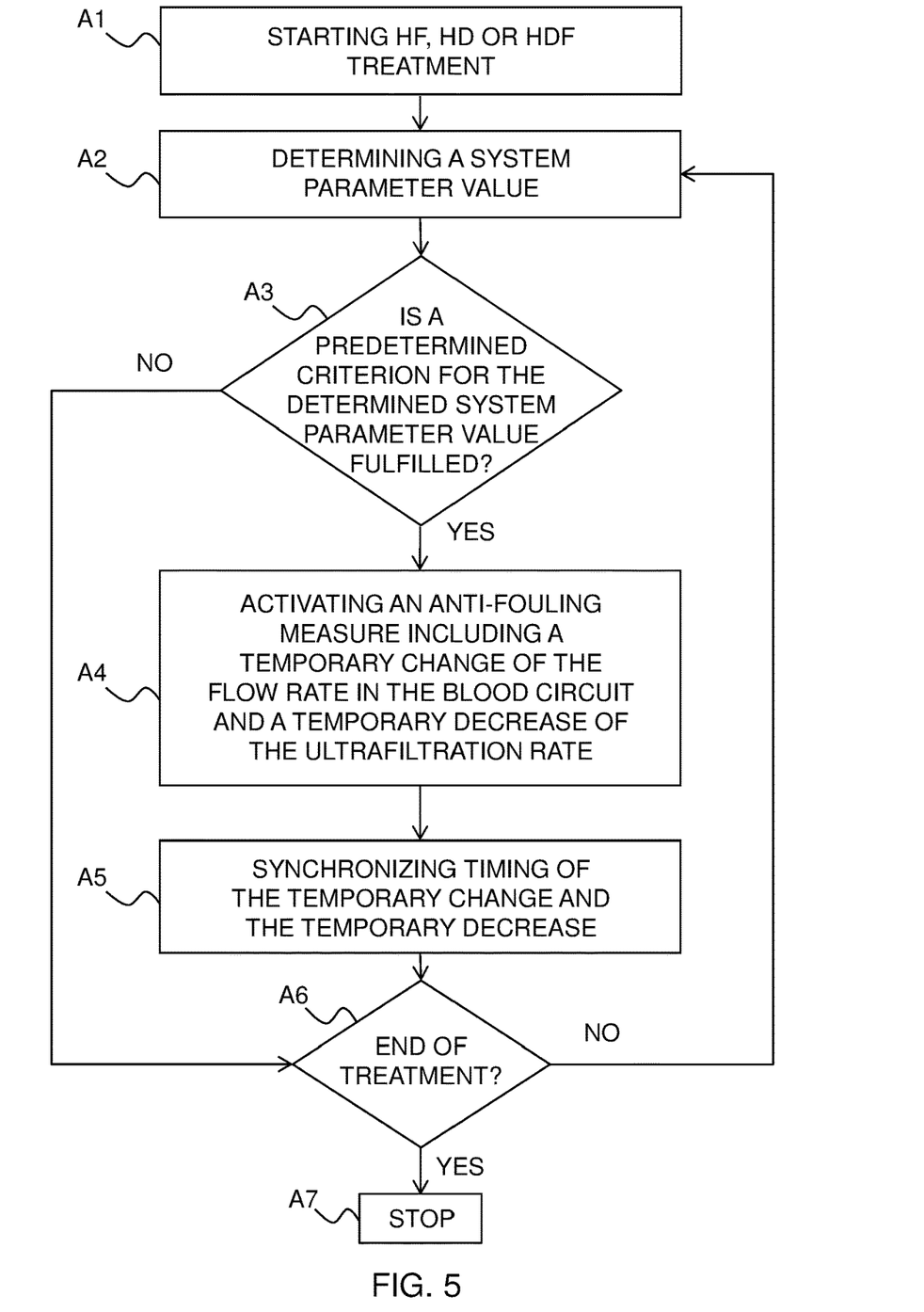
FIG. 5 illustrates a method for a renal replacement treatment system according to one embodiment.

The method will now be described with reference to the flowchart in FIG. 5, and to the system illustration in FIG. 1. Before the present method is activated, a treatment in UF, HF, HD or HDF has started and is ongoing. Also, in HF or HDF the treatments may be performed with post-dilution (A1). During the treatment, the method comprises determining a system parameter value (A2). The system parameter value may be a value of any of the herein described system parameters.

The method further comprises determining an indication of membrane fouling of the membrane 7 based on the predetermined criterion for the determined system parameter value (A3). The criterion may comprise a limit value for the system parameter. In response to determining such an indication, where the predetermined criterion is fulfilled, the method continues with activating an automatic anti-fouling measure as has been previously described (A4). If the criterion is not fulfilled, and the treatment is not ended (A5), the method returns to step A2. The anti-fouling measure comprises temporarily changing the flow rate in the blood circuit 2 upstream the blood treatment unit 4 and temporarily decreasing an ultrafiltration rate across the semipermeable membrane 7 (A4). The flow rate in the blood circuit 2 may be temporary changed by infusing a volume of substitution fluid via the pre-dilution line 10 to the blood circuit 2. The flow rate in the blood circuit 2 will then be correspondingly temporarily increased. Alternatively the temporary change of the flow rate in the blood circuit 2 comprises increasing, decreasing or stopping the velocity of the blood pump 19. The flow rate in the blood circuit 2 will then be correspondingly temporarily increased, decreased or stopped. The flow rate in the blood circuit 2 may also be increased by the infusion of substitution fluid and simultaneously decreasing or stopping the blood flow rate by decreasing or stopping the velocity of the blood pump 19. The resulting flow rate in the blood circuit 2 is then a sum of the changes, and the blood concentration will be changed. The current flow rate of the pre-dilution flow rate $Q_{pre}$ may be zero, thus, the pre-dilution flow rate $Q_{pre}$ may increase from zero flow rate. The anti-fouling measure may comprise temporarily stopping the post-dilution flow rate $Q_{post}$, if any, during some of or whole of the at least one time period $\Delta t1$. The anti-fouling measure further comprises synchronizing timing of the temporary change of the flow rate in the blood circuit 2 and timing of the temporary decreasing of the ultrafiltration rate (A5). This comprises to determine at what time the temporary change of the flow rate in the blood circuit 2 shall occur, and to determine at what time the temporary reduction of the flow rate in the dialysis fluid circuit 3 shall occur, such that a desired anti-fouling effect is obtained. The order and length of the temporary change or changes, and temporary reduction may be predetermined and saved in the memory unit 33. That is, the time periods $\Delta t1$, $\Delta t2$, $\Delta t3$ and/or $\Delta t4$, and their order and timing in relation to each other may be predetermined and saved in the memory unit 33.

The synchronizing comprises to synchronize the timing such that the infusion or infusions of the volume or volumes of dialysis fluid is/are performed during the at least one time period $\Delta t2$.

In order to synchronize the timing, the method may comprise controlling timing of the temporary change of the flow rate in the blood circuit 2 and controlling the timing of the temporary decreasing of the ultrafiltration rate such that the temporary change of the flow rate in the blood circuit 2 and the temporary decreasing of the ultrafiltration rate have an impact on the blood treatment unit 4 simultaneously during at least one time period $\Delta t2$.

For example, the method may comprise controlling timing of the temporary change of the flow rate in the blood circuit 2 and controlling timing of the temporary decreasing of the ultrafiltration rate such that the temporary decreasing of the ultrafiltration rate has an earlier impact on the blood treatment unit 4 than the impact the temporary change of the flow rate in the blood circuit 2 has to the blood treatment unit 4. The temporary change of the flow rate in the dialysis fluid circuit 3 may then be started, that is activated, the time period $\Delta t3$ before the start of the temporary change of the flow rate in the blood circuit 2.

The method may alternatively comprise controlling timing of the temporary change of the flow rate in the blood circuit 2 and controlling timing of the temporary decreasing of the ultrafiltration rate such that the temporary change of the flow rate in the blood circuit 2 at least partly has an earlier impact on the blood treatment unit 4 than the impact of the temporary decreasing of the ultrafiltration rate has to the blood treatment unit 4. The temporary change of the flow rate in the blood circuit 2 may then be started, that is activated, the time period Δt3 before the temporary change of the flow rate in the dialysis fluid circuit 3.

According to some embodiments, the method comprises controlling the ultrafiltration rate after an anti-fouling measure, such that the temporary decrease of the ultrafiltration rate across the semipermeable membrane 7 is compensated for during the remaining treatment. This may be accomplished by regulating the ultrafiltration rate such that the predetermined volume to be withdrawn from the patient is actually withdrawn during the remaining treatment, e.g. by increasing the ultrafiltration rate. This may comprise compensating for any infused volume during backwash.

The system parameter value based on one or several of UFR, $C_E$, TMP, $Q_{IR}$, $Q_{pre}$, $Q_{post}$, $P_{bi}$, UF coefficient, current $I_B$ of the motor 37 of the blood pump 19, or another efficiency parameter of the treatment may indicate membrane fouling of the membrane 7 according to the method, and the anti-fouling measure may be controlled based on the determined system parameter value. The predetermined criterion may comprise a limit value of the value of the system parameter. The method may comprise comparing the determined system parameter value with the limit value of the system parameter, and controlling the anti-fouling measure based on a result of the comparison. The method may also comprise comparing the determined clearance value K or conductivity of the waste fluid with a limit value of the clearance parameter or conductivity, respectively, and controlling the anti-fouling measure based on a result of the comparison. The method may comprise maintaining the automatic anti-fouling measure for a certain time period Δt1 after activation of the same, e.g. based on the result of the comparison. For example, if the system parameter value exceeds its limit value with a large amount, the time period Δt1 may be longer than if the system parameter value exceeds its limit value with a small amount. The method may comprise monitoring parameter values over time and calculating a change or changes of one or several of the parameters in Δ-values, for example: $\Delta P_{bi}$, $\Delta P_{bo}$, $\Delta P_{di}$, $\Delta P_{do}$, $\Delta Q_{di}$, $\Delta Q_{drain}$, $\Delta C_E$, $\Delta Q_B$, $\Delta Q_{di}$, $\Delta Q_{drain}$, ΔWLR, ΔUFR, $\Delta Q_{IR}$, $\Delta Q_{pre}$, $\Delta Q_{post}$, $\Delta I_B$, ΔTMP, ΔK, ΔUF coefficient, ΔUFR. The system parameter value may thus be a change of a certain parameter over time. The method may also comprise determining values for different system parameters, and determining an indication of membrane fouling based on a predetermined criterion each for a plurality of different system parameter values. At least one, a subset of, or all of the system parameter values must then indicate membrane fouling of the membrane in order to activate the automatic anti-fouling measure.

The temporary decrease of the ultrafiltration rate comprised in the anti-fouling measure may comprise performing a backwash of the membrane 7 of the treatment unit 4 (FIG. 1) as has been previously explained. The backwash comprises infusing a volume of dialysis fluid to the blood treatment unit 4 in order to enhance the flushing effect on the membrane 7. This means that one or several volumes of dialysis fluid may be infused from the fluid compartment 6 into the blood compartment 5 through the semipermeable membrane 7.

While the invention has been described in connection with what is presently considered to be the most practical and preferred embodiment, it is to be understood that the invention is not to be limited to the disclosed embodiments, but on the contrary, is intended to cover various modifications and equivalent arrangements comprised within the scope of the appended claims.

The invention claimed is:

1. A system for renal replacement therapy comprising:
   a blood treatment unit arranged to be connected to a blood circuit for extracorporeal circulation of blood, the blood circuit including an arterial line and a venous line, and the blood treatment unit including a blood compartment and a fluid compartment separated by a semipermeable membrane;
   a blood pump arranged to create a blood flow rate in the arterial line;
   a dialysis fluid circuit including a supply line arranged for supply of a dialysis fluid to the fluid compartment of the blood treatment unit, and a drain line arranged for withdrawal of used fluid from the fluid compartment of the blood treatment unit;
   at least one fluid pump arranged to create a fluid flow rate in the dialysis fluid circuit; and
   a control unit configured to
      determine a system parameter value,
      determine an indication of membrane fouling of the semipermeable membrane based on a predetermined criterion for the system parameter value, and
      activate an anti-fouling measure in response to determining the indication of membrane fouling,
      wherein the anti-fouling measure includes a temporary change of the blood flow rate in the blood circuit upstream the blood treatment unit caused by adjusting the blood pump and a temporary decrease of an ultrafiltration rate across the semipermeable membrane caused by adjusting the at least one dialysis fluid circuit fluid pump, such that the pressure in the fluid compartment is increased, and
      wherein a timing of the temporary change of the blood flow rate in the blood circuit and a timing of the temporary decrease of the ultrafiltration rate are synchronized.

2. The system according to claim 1, wherein the predetermined criterion includes a limit value of the system parameter value, and the control unit is configured to compare the determined system parameter value with the limit value of the system parameter, and to control the anti-fouling measure based on a result of the comparison.

3. The system according to claim 1, wherein the control unit is configured to maintain the anti-fouling measure for a predetermined time period after activating the anti-fouling measure.

4. The system according to claim 1, further comprising a pre-dilution line arranged for infusion of substitution fluid upstream of the treatment unit, and a flow control device configured to regulate a pre-dilution flow rate of substitution fluid in the pre-dilution line, wherein the temporary change of the blood flow rate in the blood circuit includes infusing a volume of substitution fluid via the pre-dilution line into the blood circuit.

5. The system according to claim 1, wherein the temporary change of the blood flow rate in the blood circuit includes decreasing or stopping a velocity of the blood pump.

6. The system according to claim 1, wherein the temporary change of the blood flow rate in the blood circuit includes increasing a velocity of the blood pump.

7. The system according to claim 1, wherein the temporary decrease of the ultrafiltration rate across the semipermeable membrane is adapted to cause a backwash, and wherein the backwash includes infusing a volume of dialysis fluid from the fluid compartment into the blood compartment through the semipermeable membrane.

8. The system according to claim 1, wherein the temporary decrease of the ultrafiltration rate across the semipermeable membrane causes the ultrafiltration rate to be zero.

9. The system according to claim 1, wherein the control unit is configured to control the ultrafiltration rate after an anti-fouling measure is activated, such that the temporary decrease of the ultrafiltration rate across the semipermeable membrane is compensated for during the remaining treatment.

10. The system according to claim 1, wherein the control unit is configured to control the timing of the temporary change of the blood flow rate in the blood circuit and to control the timing of the temporary decrease of the ultrafiltration rate such that the temporary change in the blood flow rate in the blood circuit and the temporary decrease of the ultrafiltration rate have an impact on the blood treatment unit simultaneously during at least one time period.

11. The system according to claim 1, wherein the control unit is configured to control the timing of the temporary change of the blood flow rate in the blood circuit and to control the timing of the temporary decrease of the ultrafiltration rate such that the temporary decrease of the ultrafiltration rate has an earlier impact on the blood treatment unit than the temporary change of the blood flow rate in the blood circuit.

12. The system according claim 1, wherein the control unit is configured to control the timing of the temporary change of the blood flow rate in the blood circuit and to control the timing of the temporary decrease of the ultrafiltration rate such that the temporary change of the blood flow rate in the blood circuit has an earlier impact on the blood treatment unit than the temporary decrease of the ultrafiltration rate.

13. The system according to claim 1, wherein the system parameter is determined based on one or more of a current consumed by a motor of the blood pump, a system pressure, a transmembrane pressure across the blood treatment unit, an infusion flow rate, a post-dilution flow rate, a haemoconcentration of the blood, an ultrafiltration coefficient, and a clearance.

14. A method for use in a renal replacement therapy system including a blood treatment unit arranged to be connected to a blood circuit for extracorporeal circulation of blood, the blood circuit including an arterial line and a venous line, and the blood treatment unit including a blood compartment and a fluid compartment separated by a semipermeable membrane, a blood pump arranged to create a blood flow rate in the arterial line, a dialysis fluid circuit including a supply line arranged for supply of a dialysis fluid to the fluid compartment of the blood treatment unit, and a drain line arranged for withdrawal of used fluid from the fluid compartment of the blood treatment unit, at least one fluid pump arranged to create a fluid flow rate in the dialysis fluid circuit, and a control unit, the method comprising:
determining a system parameter value;
determining an indication of membrane fouling of the semipermeable membrane based on a predetermined criterion for the system parameter value; and
activating an anti-fouling measure in response to determining the indication of membrane fouling, wherein the anti-fouling measure includes a temporary change of the blood flow rate in the blood circuit upstream the blood treatment unit caused by adjusting the blood pump and a temporary decrease of an ultrafiltration rate across the semipermeable membrane caused by adjusting the at least one dialysis fluid circuit fluid pump, such that the pressure in the fluid compartment is increased,
wherein a timing of the temporary change of the blood flow rate in the blood circuit and a timing of the temporary decrease of the ultrafiltration rate are synchronized.

15. The method according to claim 14, wherein the predetermined criterion includes a limit value of the system parameter value, and the method comprises comparing the determined system parameter value with the limit value of the system parameter, and controlling the anti-fouling measure based on a result of the comparison.

16. The method according to claim 14, further comprising maintaining the anti-fouling measure for a predetermined time period after activating the anti-fouling measure.

17. The method according to claim 14, wherein the temporary change of the blood flow rate in the blood circuit includes infusing a volume of substitution fluid via a pre-dilution line into the blood circuit upstream of the treatment unit.

18. The method according to claim 14, wherein the temporary change of the blood flow rate in the blood circuit includes decreasing or stopping a velocity of the blood pump.

19. The method according to claim 14, wherein the temporary change of the blood flow rate in the blood circuit includes increasing a velocity of the blood pump.

20. The method according to claim 14, wherein the temporary decrease of the ultrafiltration rate across the semipermeable membrane is adapted to cause a backwash, wherein the backwash includes infusing a volume of dialysis fluid from the fluid compartment into the blood compartment through the semipermeable membrane.

21. The method according to claim 14, wherein the temporary decrease of the ultrafiltration rate across the semipermeable membrane causes the ultrafiltration rate to be zero.

22. The method according to claim 14, comprising controlling the ultrafiltration rate after an anti-fouling measure is activated such that the temporary decrease of the ultrafiltration rate across the semipermeable membrane is compensated for during the remaining treatment.

23. The method according to claim 14, comprising controlling the timing of the temporary change of the blood flow rate in the blood circuit and the timing of the temporary decrease of ultrafiltration rate such that the temporary change in the blood flow rate in the blood circuit and the temporary decrease of ultrafiltration rate have an impact on the blood treatment unit simultaneously during at least one time period.

24. The method according to claim 14, comprising controlling the timing of the temporary change of the blood flow rate in the blood circuit and the timing of the temporary decrease of the ultrafiltration rate such that the temporary decrease of the ultrafiltration rate has an earlier impact on the blood treatment unit than the temporary change of the blood flow rate in the blood circuit.

25. The method according to claim 14, comprising controlling the timing of the temporary change of the blood flow rate in the blood circuit and the timing of the temporary decrease of the ultrafiltration rate such that the temporary change of the blood flow rate in the blood circuit has an earlier impact on the blood treatment unit than the temporary decrease of the ultrafiltration rate.

26. The method according to claim 14, wherein the system parameter is determined based on one or more of a current consumed by a motor of the blood pump, a system pressure, a transmembrane pressure across the blood treatment unit, an infusion flow rate, a post-dilution flow rate, a haemoconcentration of the blood, an ultrafiltration coefficient, and a clearance.

27. A non-transitory computer-readable medium storing instructions for use in a renal replacement therapy system including a blood treatment unit arranged to be connected to a blood circuit for extracorporeal circulation of blood, the blood circuit including an arterial line and a venous line, and the blood treatment unit including a blood compartment and a fluid compartment separated by a semipermeable membrane, a blood pump arranged to create a blood flow rate in the arterial line, a dialysis fluid circuit including a supply line arranged for supply of a dialysis fluid to the fluid compartment of the blood treatment unit, and a drain line arranged for withdrawal of used fluid from the fluid compartment of the blood treatment unit, at least one fluid pump arranged to create a fluid flow rate in the dialysis fluid circuit, wherein the instructions, when executed by a processor, cause the processor to:
  determine a system parameter value;
  determine an indication of membrane fouling of the semipermeable membrane based on a predetermined criterion for the system parameter value; and
  activate an anti-fouling measure in response to determining the indication of membrane fouling,
  wherein the anti-fouling measure includes a temporary change of the blood flow rate in the blood circuit upstream the blood treatment unit caused by adjusting the at least one blood pump and a temporary decrease of an ultrafiltration rate across the semipermeable membrane caused by adjusting the at least one dialysis fluid circuit fluid pump, such that the pressure in the fluid compartment is increased, and
  wherein a timing of the temporary change of the blood flow rate in the blood circuit and a timing of the temporary decrease of the ultrafiltration rate are synchronized.

28. A system for renal replacement therapy comprising:
  a blood treatment unit arranged to be connected to a blood circuit for extracorporeal circulation of blood, the blood circuit including an arterial line and a venous line, and the blood treatment unit including a blood compartment and a fluid compartment separated by a semipermeable membrane;
  a blood pump arranged to create a blood flow rate in the arterial line;
  a dialysis fluid circuit including a supply line arranged for supply of a dialysis fluid to the fluid compartment of the blood treatment unit, and a drain line arranged for withdrawal of used fluid from the fluid compartment of the blood treatment unit;
  at least one fluid pump arranged to create a fluid flow rate in the dialysis fluid circuit;
  a pre-dilution line; and
  a control unit configured to
    determine a system parameter value,
    determine an indication of membrane fouling of the semipermeable membrane based on a predetermined criterion for the system parameter value, and
    activate an anti-fouling measure in response to determining the indication of membrane fouling,
  wherein the anti-fouling measure includes a temporary change of the blood flow rate in the blood circuit upstream the blood treatment unit caused by infusing a volume of substitution fluid via the pre-dilution line into the arterial line, and wherein the anti-fouling measure further includes a temporary decrease of an ultrafiltration rate across the semipermeable membrane caused by adjusting the at least one dialysis fluid circuit fluid pump, and
  wherein a timing of the temporary change of the blood flow rate in the blood circuit and a timing of the temporary decrease of the ultrafiltration rate are synchronized.

* * * * *